(12) United States Patent
Lara Gutierrez et al.

(10) Patent No.: US 11,092,606 B2
(45) Date of Patent: Aug. 17, 2021

(54) SUPER RESOLUTION IMAGING OF PROTEIN-PROTEIN INTERACTIONS

(71) Applicant: President and Fellows of Harvard College, Cambridge, MA (US)

(72) Inventors: Juanita M. Lara Gutierrez, Brookline, MA (US); Maier S. Avendano Amado, Brookline, MA (US); Peng Yin, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 165 days.

(21) Appl. No.: 15/229,759

(22) Filed: Aug. 5, 2016

(65) Prior Publication Data

US 2017/0038391 A1    Feb. 9, 2017

Related U.S. Application Data

(60) Provisional application No. 62/202,327, filed on Aug. 7, 2015.

(51) Int. Cl.
```
C12Q 1/68        (2018.01)
G01N 33/68       (2006.01)
G01N 33/58       (2006.01)
C12Q 1/6897      (2018.01)
C12Q 1/6816      (2018.01)
```
(52) U.S. Cl.
CPC ....... *G01N 33/6845* (2013.01); *C12Q 1/6816* (2013.01); *C12Q 1/6897* (2013.01); *G01N 33/582* (2013.01); *G01N 2458/10* (2013.01)

(58) Field of Classification Search
USPC .............. 435/6.1, 6.11, 6.12, 7.1, 91.1, 91.2, 435/91.51; 436/94, 501; 536/23.1, 24.3, 536/24.33, 25.3; 530/300, 350; 424/130.1
See application file for complete search history.

(56) References Cited

U.S. PATENT DOCUMENTS

| | | | |
|---|---|---|---|
| 5,424,413 A * | 6/1995 | Hogan | ............... C12N 15/1068 435/6.1 |
| 6,083,486 A | 7/2000 | Weissleder et al. | |
| 6,150,173 A | 11/2000 | Schubert | |
| 6,451,588 B1 * | 9/2002 | Egholm | ............... C12Q 1/6818 435/287.1 |
| 6,534,041 B1 | 3/2003 | Licha et al. | |

(Continued)

FOREIGN PATENT DOCUMENTS

| | | |
|---|---|---|
| DE | 4421891 A1 | 1/1996 |
| JP | H 07-503139 A | 4/1995 |

(Continued)

OTHER PUBLICATIONS

"Stringency" from GenScript. Printed on Jun. 26, 2020.*

(Continued)

*Primary Examiner* — Frank W Lu
(74) *Attorney, Agent, or Firm* — Wolf, Greenfield & Sacks, P.C.

(57) ABSTRACT

This disclosure provides methods and compositions for detecting intramolecular and intermolecular interactions, such as protein-protein interactions. These methods detect such interactions at sub-diffraction distances, and thus are referred to as super-resolution detection and imaging methods.

20 Claims, 7 Drawing Sheets

Specification includes a Sequence Listing.

(56) References Cited

U.S. PATENT DOCUMENTS

| | | | |
|---|---|---|---|
| 6,815,164 B2* | 11/2004 | Kurn | C12Q 1/6818 |
| | | | 435/6.1 |
| 6,833,246 B2 | 12/2004 | Balasubramanian | |
| 6,924,115 B2 | 8/2005 | Schubert | |
| 9,944,972 B2 | 4/2018 | Yin et al. | |
| 10,006,917 B2 | 6/2018 | Dai et al. | |
| 10,041,108 B2 | 8/2018 | Barish et al. | |
| 2002/0015679 A1 | 2/2002 | Kotov | |
| 2002/0106648 A1 | 8/2002 | Lizardi et al. | |
| 2002/0173053 A1 | 11/2002 | Damaj et al. | |
| 2002/0177149 A1 | 11/2002 | Rimm et al. | |
| 2003/0044353 A1 | 3/2003 | Weissleder et al. | |
| 2003/0064398 A1 | 4/2003 | Barnes | |
| 2003/0073149 A1 | 4/2003 | Archer et al. | |
| 2004/0121382 A1 | 6/2004 | Liu et al. | |
| 2004/0121385 A1 | 6/2004 | Andersson et al. | |
| 2004/0248325 A1 | 12/2004 | Bukusoglu | |
| 2005/0014163 A1* | 1/2005 | Dong | C12Q 1/6832 |
| | | | 435/6.1 |
| 2005/0095595 A1* | 5/2005 | Pittaro | C12Q 1/6837 |
| | | | 435/6.11 |
| 2005/0169843 A1 | 8/2005 | Weissleder et al. | |
| 2005/0171434 A1 | 8/2005 | Madden et al. | |
| 2005/0287578 A1 | 12/2005 | Davis | |
| 2006/0204999 A1 | 9/2006 | Macevicz | |
| 2007/0048759 A1 | 3/2007 | Luo et al. | |
| 2007/0117109 A1 | 5/2007 | Rothemund | |
| 2008/0044834 A1 | 2/2008 | Heyduk | |
| 2008/0182336 A1 | 7/2008 | Zhuang et al. | |
| 2009/0011956 A1 | 1/2009 | Yin et al. | |
| 2010/0068710 A1* | 3/2010 | Buela | C12Q 1/6827 |
| | | | 435/6.11 |
| 2010/0081134 A1 | 4/2010 | Mirkin et al. | |
| 2010/0151472 A1 | 6/2010 | Nolan et al. | |
| 2011/0244457 A1* | 10/2011 | Nadeau | C12Q 1/6804 |
| | | | 435/6.11 |
| 2012/0071330 A1 | 3/2012 | Kokoris et al. | |
| 2012/0107798 A1 | 5/2012 | Santangelo | |
| 2012/0178081 A1 | 7/2012 | Nguyen et al. | |
| 2013/0027518 A1 | 1/2013 | Mackay et al. | |
| 2014/0248710 A1 | 9/2014 | Heyduk et al. | |
| 2014/0256588 A1 | 9/2014 | Glezer et al. | |
| 2016/0033411 A1 | 2/2016 | Barish et al. | |
| 2016/0161472 A1 | 6/2016 | Jungmann et al. | |
| 2016/0169903 A1 | 6/2016 | Dai et al. | |
| 2016/0312272 A1 | 10/2016 | Barish et al. | |
| 2016/0319328 A1 | 11/2016 | Yin et al. | |
| 2017/0137864 A1 | 5/2017 | Yin et al. | |
| 2018/0037950 A1* | 2/2018 | Gunderson | B01J 19/0046 |
| 2018/0216159 A1 | 8/2018 | Yin et al. | |
| 2018/0224461 A1 | 8/2018 | Gutierrez et al. | |
| 2019/0323061 A1 | 10/2019 | Yin et al. | |
| 2020/0064340 A1 | 2/2020 | Jungmann et al. | |

FOREIGN PATENT DOCUMENTS

| | | |
|---|---|---|
| JP | 2004-537257 A | 12/2004 |
| WO | WO 98/18961 A1 | 5/1998 |
| WO | WO 00/03034 A2 | 1/2000 |
| WO | WO 00/20641 A1 | 4/2000 |
| WO | WO 00/58507 A1 | 10/2000 |
| WO | WO 02/079771 A1 | 10/2002 |
| WO | WO 2004/009848 A1 | 1/2004 |
| WO | WO 2005/017485 A2 | 2/2005 |
| WO | WO 2012/058638 A2 | 5/2012 |
| WO | WO 2012/071428 A2 | 5/2012 |
| WO | WO 2013/010023 A2 | 1/2013 |
| WO | WO 2014/145620 A2 | 9/2014 |
| WO | WO 2015/017586 A1 | 2/2015 |
| WO | WO 2015/089506 A2 | 6/2015 |
| WO | WO 2015/138653 A1 | 9/2015 |

OTHER PUBLICATIONS

"Hybridization probe" from Wikipedia. Printed on Jun. 26, 2020.*
Aitken et al., An oxygen scavenging system for improvement of dye stability in single-molecule fluorescence experiments. Biophys J. Mar. 1, 2008;94(5):1826-35. Epub Oct. 5, 2007.
Azcona et al., Development and clinical evaluation of automatic fiducial detection for tumor tracking in cine megavoltage images during volumetric modulated arc therapy. Med Phys. Mar. 2013;40(3):031708. doi:10.1118/1.4791646.
Baines et al., Peptide aptamers as guides for small-molecule drug discovery. Drug Discov Today. Apr. 2006;11(7-8):334-41.
Betzig et al., Imaging intracellular fluorescent proteins at nanometer resolution. Science. Sep. 15, 2006;313(5793):1642-5. Epub Aug. 10, 2006.
Bird et al., Single-chain antigen-binding proteins. Science. Oct. 21, 1988;242(4877):423-6.
Derr et al., Tug-of-war in motor protein ensembles revealed with a programmable DNA origami scaffold. Science. Nov. 2, 2012;338(6107):662-5. doi: 10.1126/science.1226734. Epub Oct. 11, 2012.
Fukusaki et al., SELEX for tubulin affords specific T-rich DNA aptamers. Bioorg Med Chem Lett. Nov. 19, 2001;11(22):2927-30.
Giannone et al., Dynamic superresolution imaging of endogenous proteins on living cells at ultra-high density. Biophys J. Aug. 9, 2010;99(4):1303-10. doi: 10.1016/j.bpj.2010.06.005.
Hein et al., Stimulated emission depletion (STED) nanoscopy of a fluorescent protein-labeled organelle inside a living cell. Proc Natl Acad Sci U S A. Sep. 23, 2008;105(38):14271-6. doi:10.1073/pnas.0807705105. Epub Sep. 16, 2008.
Hell et al., Breaking the diffraction resolution limit by stimulated emission: stimulated-emission-depletion fluorescence microscopy. Opt Lett. Jun. 1, 1994;19(11):780-2.
Hell et al., Microscopy and its focal switch. Nat Methods. Jan. 2009;6(1):24-32. doi: 10.1038/nmeth.1291.
Hu et al., Visualization of interactions among bZIP and Rel family proteins in living cells using bimolecular fluorescence complementation. Mol Cell. Apr. 2002;9(4):789-98.
Huang et al., Three-dimensional super-resolution imaging by stochastic optical reconstruction microscopy. Science. Feb. 8, 2008;319(5864):810-3. doi: 10.1126/science.1153529. Epub Jan. 3, 2008.
Huston et al., Protein engineering of antibody binding sites: recovery of specific activity in an anti-digoxin single-chain Fv analogue produced in Escherichia coli. Proc Natl Acad Sci U S A. Aug. 1988;85(16):5879-83.
Johnson-Buck et al., Super-resolution fingerprinting detects chemical reactions and idiosyncrasies of single DNA pegboards. Nano Lett. Feb. 13, 2013;13(2):728-33. doi:10.1021/nl304415b. Epub Jan. 31, 2013.
Jones et al., Fast, three-dimensional super-resolution imaging of live cells. Nat Methods. Jun. 2011;8(6):499-508. doi: 10.1038/nmeth.1605. Epub May 8, 2011.
Jungmann et al., Single-molecule kinetics and super-resolution microscopy by fluorescence imaging of transient binding on DNA origami. Nano Lett. Nov. 10, 2010;10(11):4756-61. doi: 10.1021/nl103427w.
Lew et al., Three-dimensional superresolution colocalization of intracellular protein superstructures and the cell surface in live Caulobacter crescentus. Proc Natl Acad Sci U S A. Nov. 15, 2011;108(46):E1102-10. doi: 10.1073/pnas.1114444108. Epub Oct. 26, 2011.
Lin et al., Submicrometre geometrically encoded fluorescent barcodes self-assembled from DNA. Nat Chem. Oct. 2012;4(10):832-9.
Liu et al., Super-resolution imaging and tracking of protein-protein interactions in sub-diffraction cellular space. Nat Commun. Jul. 17, 2014;5:4443. doi: 10.1038/ncomms5443.
Lubeck et al., Single-cell systems biology by super-resolution imaging and combinatorial labeling. Nat Methods. Jun. 3, 2012;9(7):743-8. doi:10.1038/nmeth.2069.
Ni et al., Nucleic acid aptamers: clinical applications and promising new horizons. Curr Med Chem. 2011;18(27):4206-14.

(56) References Cited

OTHER PUBLICATIONS

Paige et al., Fluorescence imaging of cellular metabolites with RNA. Science. Mar. 9, 2012;335(6073):1194. doi:10.1126/science.1218298.
Paige et al., RNA mimics of green fluorescent protein. Science. Jul. 29, 2011;333(6042):642-6. doi:10.1126/science.1207339.
Rasnik et al., Nonblinking and long-lasting single-molecule fluorescence imaging. Nat Methods. Nov. 2006;3(11):891-3. Epub Oct. 1, 2006.
Ries et al., A simple, versatile method for GFP-based super-resolution microscopy via nanobodies. Nat Methods. Jun. 2012;9(6):582-4. doi: 10.1038/nmeth.1991. Epub Apr. 29, 2012.
Rust et al, Sub-diffraction-limit imaging by stochastic optical reconstruction microscopy (STORM). Nat Methods. Oct. 2006;3(10):793-5. Epub Aug. 9, 2006.
Sharonov et al.,Wide-field subdiffraction imaging by accumulated binding of diffusing probes. Proc Natl Acad Sci U S A. Dec. 12, 2006;103(50):18911-6. Epub Dec. 1, 2006.
Soderberg et al., Direct observation of individual endogenous protein complexes in situ by proximity ligation. Nat Methods. Dec. 2006;3(12):995-1000. Epub Oct. 29, 2006.
Stoltenburg et al., SELEX—a (r)evolutionary method to generate high-affinity nucleic acid ligands. Biomol Eng. Oct. 2007;24(4):381-403. Epub Jun. 16, 2007.
Tokunaga et al., Highly inclined thin illumination enables clear single-molecule imaging in cells. Nat Methods. Feb. 2008;5(2):159-61. doi: 10.1038/nmeth1171. Epub Jan. 6, 2008.
Ward et al., Binding activities of a repertoire of single immunoglobulin variable domains secreted from *Escherichia coli*. Nature. Oct. 12, 1989;341(6242):544-6.
Wei et al., Complex shapes self-assembled from single-stranded DNA tiles. Nature. May 30, 2012;485(7400):623-6. doi: 10.1038/nature11075.
Willig et al., Nanoscale resolution in GFP-based microscopy. Nat Methods. Sep. 2006;3(9):721-3.
Winckler et al., Identification and super-resolution imaging of ligand-activated receptor dimers in live cells. Sci Rep. 2013;3:2387. doi: 10.1038/srep02387.
Extended European Search Report for EP 14831813.2 dated Jan. 31, 2017.
International Search Report and Written Opinion dated Dec. 28, 2016 for PCT/US2016/045756.
International Preliminary Report on Patentability dated Feb. 22, 2018 for Application No. PCT/US2016/045756.
Greenwood et al., Proximity assays for sensitive quantification of proteins. Biomol Detect Quantif. May 20, 2015;4:10-6. doi: 10.1016/j.bdq.2015.04.002. eCollection 2015.
Gullberg et al., Cytokine detection by antibody-based proximity ligation. PNAS. Jun. 1, 2004;101(22):8420-4.
Jungmann et al., Multiplexed 3D cellular super-resolution imaging with DNA-PAINT and Exchange-PAINT. Nature Methods. Mar. 2014;11(3):313-21.
Jungmann et al., Multiplexed 3D cellular super-resolution imaging with DNA-PAINT and Exchange-PAINT. Nat Methods. Mar. 2014;11(3):313-8. doi: 10.1038/nmeth.2835. Epub Feb. 2, 2014. Supplementary Text and Figures; 38 pages.
Niemeyer et al., Oligonucleotide-directed self-assembly of proteins: semisynthetic DNA-streptavidin hybrid molecules as connectors for the generation of macroscopic arrays and the construction of supramolecular bioconjugates. Nucleic Acids Research. 1994;22(25):5530-9.
Stadler et al., Fluorescent DNA nanotags featuring covalently attached intercalating dyes: Synthesis, antibody conjugation, and intracellular imaging. Bioconjug Chem. Aug. 17, 2011;22(8):1491-502. doi: 10.1021/bc100485f. Epub Jul. 22, 2011. 28 pages.
Yin et al., Kinetics and dynamics of DNA hybridization. Acct Chem Res. 2011;44(11):1172-81. Epub Jun. 30, 2011.
[No Author Listed] DNA origami scaffolds for cryo-EM visualization of membrane associated complexes. University of Michigan. Project ID: 377. Last accessed from http://mcubed.umich.edu/projects/dna-origami-scaffolds-cryo-em-visualization-membrane-associated-complexes on Nov. 12, 2015.
[No Author Listed], New England Biolabs, Inc. 2013-14 Catalog and Technical Reference, User Enzyme, 2013, p. 129.
Ahern, Biochemical, reagents kits offer scientists good return on investment. The Scientist. Jul. 24, 1995;9(15):20. 7 pages. Http://the-scientist.com/article/print/16618/.
Asanuma et al., Enantioselective Incorporation of Azobenzenes into Oligodeoxyribonucleotide for Effective Photoregulation of Duplex Formation This work was partially supported by a Grant-in-Aid for Scientific Research from the Ministry of Education, Culture, Sports, Science and Technology, Japan (Molecular Synchronization for Design of New Materials System). The support by the Grant from "Research for the Future" Program of the Japan Society for the Promotion of Science JSPS-RFTF97I00301) is also acknowledged. . Angew Chem Int Ed Engl. Jul. 16, 2001;40(14):2671-2673.
Bai et al., Cryo-EM structure of a 3D DNA-origami object. Proc Natl Acad Sci U S A. Dec. 4, 2012;109(49):20012-7. doi:10.1073/pnas.1215713109. Epub Nov. 19, 2012.
Ben-Shem et al., The structure of the eukaryotic ribosome at 3.0 Å resolution. Science. Dec. 16, 2011;334(6062):1524-9. doi: 10.1126/science.1212642. Epub Nov. 17, 2011.
Chapman et al., Femtosecond X-ray protein nanocrystallography. Nature. Feb. 3, 2011;470(7332):73-7. doi: 10.1038/nature09750.
Cheng et al., A primer to single-particle cryo-electron microscopy. Cell. Apr. 23, 2015;161(3):438-49. doi:10.1016/j.cell.2015.03.050.
Douglas et al., DNA-nanotube-induced alignment of membrane proteins for NMR structure determination. Proc Natl Acad Sci U S A. Apr. 17, 2007;104(16):6644-8. Epub Apr. 2, 2007.
Eggeling et al., Photobleaching of Fluorescent Dyes under Conditions Used for Single-Molecule Detection: Evidence of Two-Step Photolysis. Anal Chem. Jul. 1, 1998;70(13):2651-9. doi: 10.1021/ac980027p.
Fedorov et al., Modern methods for modulation and imaging of endogenous microRNA. Bulletin of Almazov Federal Heart, Blood and Endocrinology Center. Oct. 2012;5:77-81.
Fujimoto et al., Site-specific photochemical RNA editing. Chem Commun (Camb). Oct. 28, 2010;46(40):7545-7. doi:10.1039/c0cc03151h. Epub Sep. 17, 2010.
Ghauharali et al., Fluorescence photobleaching-based image standardization for fluorescence microscopy. J Microscopy. May 2000;198(2):88-100.
Jenner et al., Crystal structure of the 80S yeast ribosome. Curr Opin Struct Biol. Dec. 2012;22(6):759-67. doi:10.1016/j.sbi.2012.07.013. Epub Aug. 8, 2012. Review.
Jones et al., Nanomaterials. Programmable materials and the nature of the DNA bond. Science. Feb. 20, 2015;347(6224):1260901. doi:10.1126/science.1260901.
Kato et al., High-resolution structural analysis of a DNA nanostructure by cryoEM. Nano Lett. Jul. 2009;9(7):2747-50. doi: 10.1021/nl901265n.
Ke et al., DNA brick crystals with prescribed depths. Nat Chem. Nov. 2014;6(11):994-1002. doi: 10.1038/nchem.2083. Epub Oct. 19, 2014.
Manning et al., Fabrication of patterned surfaces by photolithographic exposure of DNA hairpins carrying a novel photolabile group. J Exp Nanoscience. Feb. 1, 2010;5(1): 26-39.
Manning et al., Use of oligonucleotides carrying photolabile groups for the control of the deposition of nanoparticles in surfaces and nanoparticle association. Int J Mol Sci. 2011;12(10):7238-49. doi: 10.3390/ijms12107238. Epub Oct. 24, 2011.
Martin, Functional Synthetic DNA Nanostructures. Dissertation. Technische Universitat Munchen, Laboratory for Biomolecular Nanotechnology. Filed on Mar. 12, 2013.
Meserve et al., A double-stranded molecular probe for homogeneous nucleic acid analysis. Analyst. Aug. 2008;133(8):1013-9. doi:10.1039/b804853c. Epub Jun. 6, 2008.
Mittag et al., Sequential photobleaching of fluorochromes for polychromatic slide-based cytometry. Cytometry A. Mar. 2006;69(3):139-41.
Nannenga et al., High-resolution structure determination by continuous-rotation data collection in MicroED. Nat Methods. Sep. 2014;11(9):927-30. doi: 10.1038/nmeth.3043. Epub Aug. 3, 2014.

(56) References Cited

OTHER PUBLICATIONS

Nannenga et al., Protein structure determination by MicroED. Curr Opin Struct Biol. Aug. 2014;27:24-31. doi: 10.1016/j.sbi.2014.03.004. Epub Apr. 5, 2014.

Pinheiro et al., Challenges and opportunities for structural DNA nanotechnology. Nat Nanotechnol. Nov. 6, 2011;6(12):763-72. doi:10.1038/nnano.2011.187.

Rodgers et al., Transient association of Ku with nuclear substrates characterized using fluorescence photobleaching. J Immunol. Mar. 1, 2002;168(5):2348-55.

Shi et al., Three-dimensional electron crystallography of protein microcrystals. Elife. Nov. 19, 2013;2:e01345. doi:10.7554/eLife.01345.

Shi, A glimpse of structural biology through X-ray crystallography. Cell. Nov. 20, 2014;159(5):995-1014. doi: 10.1016/j.cell.2014.10.051.

Wahlby et al., Sequential immunofluorescence staining and image analysis for detection of large numbers of antigens in individual cell nuclei. Cytometry. Jan. 1, 2002;47(1):32-41.

Wang et al., Caged molecular beacons: controlling nucleic acid hybridization with light. Chem Commun. 2011;47:5708-10.

Winfree et al., Design and self-assembly of two-dimensional DNA crystals. Nature. Aug. 6, 1998;394(6693):539-44.

Wlodawer et al., Protein crystallography for aspiring crystallographers or how to avoid pitfalls and traps in macromolecular structure determination. FEBS J. Nov. 2013;280(22):5705-36. doi:10.1111/febs.12495. Epub Sep. 18, 2013.

Yang et al., Nanostructures as Programmable Biomolecular Scaffolds. Bioconjug Chem. Aug. 19, 2015;26(8):1381-95. doi:10.1021/acs.bioconjchem.5b00194. Epub May 22, 2015.

Zhang et al., Structural DNA nanotechnology: state of the art and future perspective. J Am Chem Soc. Aug. 13, 2014;136(32):11198-211. doi:10.1021/ja505101a. Epub Jul. 28, 2014.

Zheng et al., From molecular to macroscopic via the rational design of a self-assembled 3D DNA crystal. Nature. Sep. 3, 2009;461(7260):74-7. doi:10.1038/nature08274.

U.S. Appl. No. 14/908,333, filed Jan. 28, 2016, Published, 2016-0161472.

PCT/US2014/048977, Nov. 5, 2014, Invitation to Pay Additional Fees.

PCT/US2014/048977, Jan. 6, 2015, International Search Report and Written Opinion.

PCT/US2014/048977, Feb. 11, 2016, International Preliminary Report on Patentability.

PCT/US2016/045756, Oct. 12, 2016, Invitation to Pay Additional Fees.

EP 16835690.5, Apr. 29, 2019, Extended European Search Report.

U.S. Appl. No. 15/104,570, filed Jun. 15, 2016, Granted, U.S. Pat. No. 10,041,108.

U.S. Appl. No. 15/108,911, filed Jun. 29, 2016, Allowed, 2016-0319328.

U.S. Appl. No. 15/410,700, filed Jan. 19, 2017, Granted, U.S. Pat. No. 9,944,972.

U.S. Appl. No. 15/934,031, filed Mar. 23, 2018, Allowed, 2018-0216159.

U.S. Appl. No. 14/742,662, filed Jun. 17, 2015, Granted, U.S. Pat. No. 10,006,917.

U.S. Appl. No. 15/750,880, filed Feb. 7, 2018, Published, 2018-0224461.

U.S. Appl. No. 16/559,490, filed Sep. 3, 2019, Published, 2020-0064340.

U.S. Appl. No. 16/357,099, filed Mar. 18, 2019, Published, 2019-0323061.

\* cited by examiner

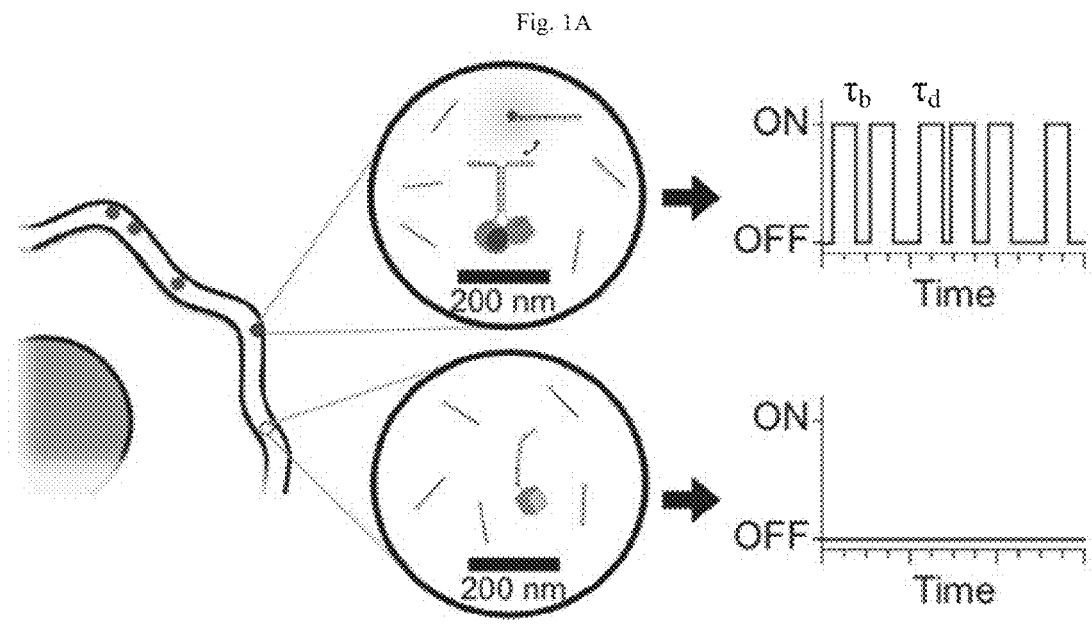
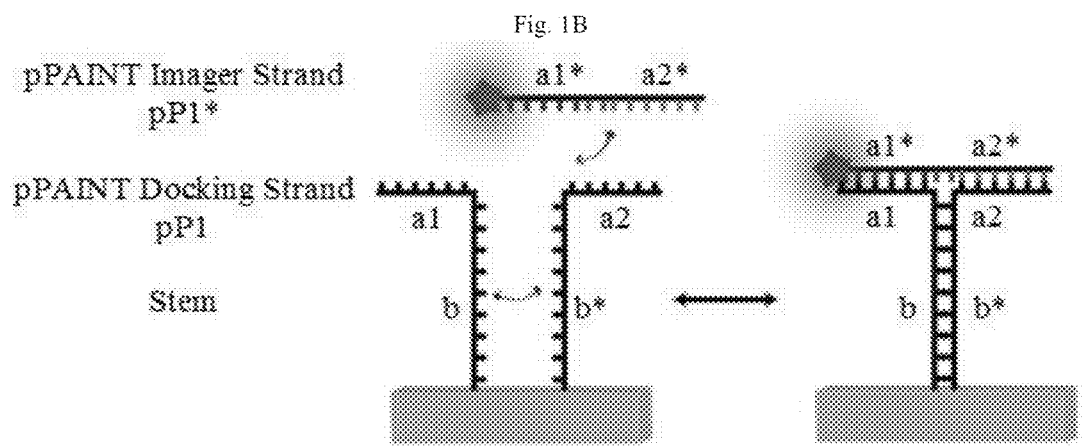

SUPER RESOLUTION IMAGING OF PROTEIN-PROTEIN INTERACTIONS

RELATED APPLICATION

This application claims the benefit under 35 U.S.C. § 119(e) of U.S. provisional application No. 62/202,327, filed Aug. 7, 2015, which is incorporated by reference herein in its entirety.

FEDERALLY SPONSORED RESEARCH

This invention was made with government support under U01-MH106011-01 and 5R01EB018659-02 awarded by National Institutes of Health and under CCF-1317291 awarded by National Science Foundation and under N00014-13-1-0593 awarded by U.S. Department of Defense, Office of Naval Research. The government has certain rights in the invention.

BACKGROUND

Genome sequencing data has produced a vast amount of predicted protein sets. The establishment of comprehensive interactome maps useful for biomedical research, however, requires precise and accurate methods to study the localization and co-localization of interacting proteins. Many of the currently available methods cannot detect transient interactions in single cells, and instead can only detect relatively stable protein interactions in cell populations (e.g., using co-immunoprecipitation).

SUMMARY

The present disclosure provides compositions, kits and methods for super-resolution imaging of interacting moieties, such as proteins and other biomolecules. These sensitive and specific methods, which build on DNA-PAINT (deoxyribonucleic acid-point accumulation for imaging in nanoscale topography) technology, are referred to herein as 'proximity DNA-PAINT' methods. Proximity DNA-PAINT is used, in some embodiments, to detect/visualize interactions between two different molecules, such as intracellular proteins (or nucleic acids) in an individual cell. Proximity DNA-PAINT uses a pair of oligonucleotides (e.g., single-stranded nucleic acids having a length of less than 200 nucleotides, or a length of less than 100 nucleotides), each oligonucleotide comprising a domain that forms half of a 'docking site' to which a labeled 'imager strand' binds only when two halves are brought together to form a full docking site. Each oligonucleotide also comprises a stability domain. The stability domains of a pair of oligonucleotides are complementary to each other such that when the pair of oligonucleotides are brought close together by interaction between the binding partners (e.g., proteins) to which the oligonucleotides are linked, the oligonucleotides bind to each other (through the stability/stem domains). The full docking site forms only when two oligonucleotides of a (complementary) pair, each containing half of the docking site, bind to each other (when two binding partners of interest interact with, or are very close to, each other), as depicted in FIGS. 1A-1B. Thus, binding of an imager strand to a docking site will only occur when both oligonucleotides of a pair are sufficiently close to each other that they bind to each other. By conjugating each pair of oligonucleotides to a pair of target-specific binding partners, such as target-specific antibodies, the interactions of such targets can be observed with sub-diffraction limit resolution directly. Thus, the compositions and methods, as provided herein, can be used to visualize interactions between endogenous proteins in individual cells, for example. Multiplexing can also be achieved through the orthogonality of DNA docking strands.

Thus, the present disclosure provides systems, compositions and kits comprising (a) a first binding partner-oligonucleotide conjugate comprising a binding partner linked to an oligonucleotide that comprises a half-docking domain, a stability domain, and optionally a spacer domain, (b) a second binding partner-oligonucleotide conjugate comprising a binding partner linked to an oligonucleotide that comprises a half-docking domain, a stability domain, and optionally a spacer domain, wherein the stability domains of (a) and (b) are complementary to each other, and wherein the half-docking domains of (a) and (b) combine linearly to form a full docking domain, and (c) an imager strand comprising a 5' domain, a 3' domain, and a linker domain located between the 5' domain and the 3'domain, wherein the 5' domain is complementary to the half-docking domain of (a) and the 3' domain is complementary to the half-docking domain of (b).

In some embodiments, each of the binding partners of (a) and (b) is an antibody or antigen-binding antibody fragment. Antibodies (and antigen-binding antibody fragments) may be, for example, monoclonal or polyclonal. Chimeric antibodies (and antigen-binding antibody fragments and humanized antibodies (and antigen-binding antibody fragments) are also encompassed herein.

In some embodiments, each of the binding partners of (a) and (b) binds to a different protein. For example, a pair of binding partners may include one antibody that binds specifically to Protein A, and another antibody that binds specifically to Protein B. Thus, each binding partner (e.g., antibody) binds to a different protein (e.g., one to Protein A, one to Protein B). In some embodiments, each of the binding partners of (a) and (b) binds to a different binding sites (e.g., epitopes) of the same protein. For example, a pair of binding partners may include one antibody that binds specifically to Epitope A of Protein A, and another antibody that binds specifically to Epitope B of Protein A. Thus, each binding partner (e.g., antibody) binds to a different epitope of the same protein (e.g., one to Epitope A, one to Epitope B).

In some embodiments, each of the half-docking domains of (a) and (b) has a length of 5-15 nucleotides. For example, each of the half-docking domains of (a) and (b) may have a length of 5-10 nucleotides. In some embodiments, each of the half-docking domains of (a) and (b) has a length of 3-20, 3-15, 3-10, 4-20, 4-15, 4-10, 5-20, 5-15 or 5-10 nucleotides. In some embodiments, each of the half-docking domains of (a) and (b) has a length of 3, 4, 5, 6, 7, 8, 9, 10, 11, 12, 13, 14, 15, 16, 17, 18, 19 or 20 nucleotides. In some embodiments, each of the half-docking domains of (a) and (b) has a length of 5±2 nucleotides, 6±2 nucleotides, 7±2 nucleotides, or 8±2 nucleotides. In some embodiments, each of the half-docking domains of (a) and (b) has a length of 5-7 nucleotides. In some embodiments, each of the half-docking domains of (a) and (b) has a length of 6 nucleotides.

In some embodiments, each of the stability domains of (a) and (b) has a length of 5-50 nucleotides. For example, each of the stability domains of (a) and (b) may have a length of 5-40, 5-30, 5-20, 5-10, 10-50, 10-40, 10-30 or 10-20 nucleotides. In some embodiments, each of the stability domains of (a) and (b) has a length of 5, 6, 7, 8, 9, 10, 11, 12, 13, 14, 15, 16, 17, 18, 19 or 20 nucleotides. In some embodiments, each of the stability domains of (a) and (b) has a length of 8±2 nucleotides, 9±2 nucleotides, 10±2 nucleotides, 11±2 nucleotides, or 12±2 nucleotides. In some embodiments, each of the stability domains of (a) and (b) has a length 9-11 nucleotides.

In some embodiments, the imager strand has a length of 10-30 nucleotides. For example, the imager strand may have a length of 10-15 or 10-20 nucleotides. In some embodiments, the imager strand has a length of 8, 9, 10, 11, 12, 13, 14, 15, 16, 17, 18, 19 or 20 nucleotides. In some embodiments, the imager strand has a length of 8±2 nucleotides, 9±2 nucleotides, 10±2 nucleotides, 11±2 nucleotides, 12±2 nucleotides, 13±2 nucleotides, 14±2 nucleotides, 15±2 nucleotides, or 16±2 nucleotides. In some embodiments, the imager strand has a length of 10-12 nucleotides or 12-14 nucleotides.

In some embodiments, each of the 5' domain and 3' domain of the imager strand has a length of 5-10 nucleotides. In some embodiments, each of the 5' domain and 3' domain of the imager strand has a length of 5, 6, 7, 8, 9 or 10 nucleotides. In some embodiments, each of the 5' domain and 3' domain of the imager strand has a length of 6 nucleotides. In some embodiments, each of the 5' domain and 3' domain of the imager strand has a length of 6±2 nucleotides.

In some embodiments, the linker domain has a length of 1-5 nucleotides. For example, the linker domain may have a length of 1, 2, 3, 4, or 5 nucleotides. In some embodiments, the linker domain comprises or consists of thymine (T) nucleotides (T residues). In some embodiments, the linker comprises or consists of a TT sequence. In some embodiments, the linker domain comprises or consists of adenine (A) nucleotides (A residues). In some embodiments, the linker comprises or consists of a AA sequence. In some embodiments, the linker domain comprises or consists of cytosine (C) nucleotides (C residues). In some embodiments, the linker comprises or consists of a CC sequence. In some embodiments, the linker domain comprises or consists of guanine (G) nucleotides (G residues). In some embodiments, the linker comprises or consists of a GG sequence.

In some embodiments, the imager strand is detectably labeled (comprises a molecule that can be detected). In some embodiments, the imager strand is fluorescently labeled (comprises a fluorescent label/molecule, such as a fluorophore).

In some embodiments, each of the binding partners of (a) and (b) is respectively conjugated to the oligonucleotide of (a) and (b) via a streptavidin-biotin binding pair. For example, a binding partner may be linked to streptavidin, and the oligonucleotide may be linked to biotin. Alternatively, a binding partner may be linked to biotin, and the oligonucleotide may be linked to streptavidin.

In some embodiments, a composition further comprises a complex that comprises two targets (e.g., proteins that bind or otherwise interact with each other), wherein the binding partner of (a) binds or is bound to one of the two targets, and the binding partner of (b) binds or is bound to the other of the two targets.

In some embodiments, each of the two targets is a protein.

In some embodiments, the imager strands of different compositions within the plurality comprise spectrally-distinct labels (e.g., some fluorescing in a red channel, others fluorescing in a blue channel, etc.).

Also provided herein is plurality (e.g., 10, 100, 1000, 10000, etc.) of compositions comprising (a) a first binding partner-oligonucleotide conjugate comprising a binding partner linked to an oligonucleotide that comprises a half-docking domain, a stability domain, and optionally a spacer domain, (b) a second binding partner-oligonucleotide conjugate comprising a binding partner linked to an oligonucleotide that comprises a half-docking domain, a stability domain, and optionally a spacer domain, wherein the stability domains of (a) and (b) are complementary to each other, and wherein the half-docking domains of (a) and (b) combine linearly to form a full docking domain, and (c) an imager strand comprising a 5' domain, a 3' domain, and a linker domain located between the 5' domain and the 3'domain, wherein the 5' domain is complementary to the half-docking domain of (a) and the 3' domain is complementary to the half-docking domain of (b), wherein the imager strands of different compositions within the plurality comprise spectrally-indistinct labels.

Also provided herein is plurality of compositions comprising (a) a first binding partner-oligonucleotide conjugate comprising a binding partner linked to an oligonucleotide that comprises a half-docking domain, a stability domain, and optionally a spacer domain, (b) a second binding partner-oligonucleotide conjugate comprising a binding partner linked to an oligonucleotide that comprises a half-docking domain, a stability domain, and optionally a spacer domain, wherein the stability domains of (a) and (b) are complementary to each other, and wherein the half-docking domains of (a) and (b) combine linearly to form a full docking domain, and (c) an imager strand comprising a 5' domain, a 3' domain, and a linker domain located between the 5' domain and the 3'domain, wherein the 5' domain is complementary to the half-docking domain of (a) and the 3' domain is complementary to the half-docking domain of (b), wherein at least one of the compositions of the plurality has a blinking frequency (e.g., $K_{ON}/K_{OFF}$) that is distinct from other compositions in the plurality.

Further provided herein are methods of detecting a complex of two targets in a sample, the methods comprising: contacting a sample with (a) a first binding partner-oligonucleotide conjugate comprising a binding partner linked to an oligonucleotide that comprises a half-docking domain, a stability domain, and optionally a spacer domain, (b) a second binding partner-oligonucleotide conjugate comprising a binding partner linked to an oligonucleotide that comprises a half-docking domain, a stability domain, and optionally a spacer domain, wherein the stability domains of (a) and (b) are complementary to each other, and wherein the half-docking domains of (a) and (b) combine linearly to form a full docking domain, and (c) an imager strand comprising a 5' domain, a 3' domain, and a linker domain located between the 5' domain and the 3'domain, wherein the 5' domain is complementary to the half-docking domain of (a) and the 3' domain is complementary to the half-docking domain of (b), wherein the binding partner of (a) has specificity for one of the two targets, and the binding partner of (b) has specificity for the other of the two targets; and detecting presence or absence of the complex in the sample.

In some embodiments, the sample is a cell (e.g., bacterial cell, yeast cell, insect cell or mammalian cell) or cell lysate.

In some embodiments, each of the two targets is a protein.

In some embodiments, each of the two targets is obtained from (e.g., isolated from or purified from) a cell or cell lysate.

In some embodiments, the methods further comprise detecting a plurality of complexes of two targets in the sample. In some embodiments, the plurality of complexes is a plurality of different complexes. In some embodiments, a subset of complexes within the plurality is located within a sub-diffraction distance of each other.

The present disclosure also provides methods of detecting an intramolecular interaction in a sample, the method comprising contacting a sample that comprises a target molecule with (a) a first binding partner-oligonucleotide conjugate comprising a binding partner linked to an oligonucleotide that comprises a half-docking domain, a stability domain, and optionally a spacer domain, wherein the binding partner of (a) has specificity for one location on a target molecule, (b) a second binding partner-oligonucleotide conjugate comprising a binding partner linked to an oligonucleotide that comprises a half-docking domain, a stability domain, and optionally a spacer domain, wherein the binding partner of (b) has specificity for another location on the target molecule, wherein the stability domains of (a) and (b) are complementary to each other, and wherein the half-docking domains of (a) and (b) combine linearly to form a full docking domain, and (c) a imager strand comprising a detectable label, a 5' domain, a 3' domain, and a linker domain located between the 5' domain and the 3'domain, wherein the 5' domain is complementary to the half-docking domain of (a) and the 3' domain is complementary to the half-docking domain of (b); and detecting presence or absence of the detectable label of the imager strand of (c) in the sample.

In some embodiments, the sample is a cell or cell lysate.

In some embodiments, the target molecule is a protein.

In some embodiments, each of the location of (a) and (b) is a different epitope on the protein. Thus, the methods may be used to detect the presence of two different binding sites (e.g., epitopes) on a protein of interest.

Also provided herein are systems, kits and compositions comprising (a) a first binding partner-oligonucleotide conjugate comprising a binding partner linked to an oligonucleotide that comprises a half-docking domain, a stability domain, and optionally a spacer domain, (b) a second binding partner-oligonucleotide conjugate comprising a binding partner linked to an oligonucleotide that comprises a half-docking domain, a stability domain, and optionally a spacer domain, wherein the stability domains of (a) and (b) are complementary to each other, and wherein the half-docking domains of (a) and (b) combine linearly to form a first full docking domain, (c) a third binding partner-oligonucleotide conjugate comprising a binding partner linked to an oligonucleotide that comprises a half-docking domain, a stability domain, and optionally a spacer domain, wherein the stability domains of (a) and (c) are complementary to each other, and wherein the half-docking domains of (a) and (c) combine linearly to form a second full docking domain, (d) an first imager strand comprising a 5' domain, a 3' domain, and a linker domain located between the 5' domain and the 3'domain, wherein the 5' domain of the first imager strand is complementary to the half-docking domain of (a) and the 3' domain of the first imager strand is complementary to the half-docking domain of (b), and (e) a second imager strand comprising a 5' domain, a 3' domain, and a linker domain located between the 5' domain and the 3'domain, wherein the 5' domain of the second imager strand is complementary to the half-docking domain of (a) and the 3' domain of the second imager strand is complementary to the half-docking domain of (c).

The present disclosure, in some embodiments, provides systems, compositions and kits comprising (a) a first antibody-oligonucleotide (e.g., antibody-DNA) conjugate comprising an antibody linked to an oligonucleotide that comprises a half-docking domain having a length of 5-7 nucleotides, a stability domain having a length of 9-11 nucleotides, and optionally a spacer domain, (b) a second antibody-oligonucleotide (e.g., antibody-DNA) conjugate comprising a binding partner linked to an oligonucleotide that comprises a half-docking domain having a length of 5-7 nucleotides, a stability domain having a length of 9-11 nucleotides, and optionally a spacer domain, wherein the stability domains of (a) and (b) are complementary to each other, and wherein the half-docking domains of (a) and (b) align (e.g., linearly) to form a full docking domain, and (c) an imager strand comprising a 5' domain having a length of 5-7 nucleotide, a 3' domain having a length of 5-7 nucleotides, and a linker domain having a length of 1-5 nucleotides located between the 5' domain and the 3'domain, wherein the 5' domain is complementary to the half-docking domain of (a) and the 3' domain is complementary to the half-docking domain of (b).

BRIEF DESCRIPTION OF DRAWINGS

FIGS. 1A-1E show an example of proximity-PAINT. FIG. 1A shows two target proteins, each labeled with one of the two p-PAINT DNA oligos. If the proteins interact, the interaction will be visible via DNA-PAINT. FIG. 1B shows detailed schematics of pPAINT oligos: the two oligos that serve as the docking site have a short complementary domain (stem) that will bind transiently. This domain is designed to have a longer mean bound time than the mean bound time of the imager strand. Thus, when the two oligos are sufficiently close to form a docking site the imager strand will bind the docking site with higher probability than if the two oligos were not sufficiently close to form a docking site. Without formation of a docking site, a DNA-PAINT trace is not observed. The imager strand (probe) used for pPAINT shown in this example has three domains: an end domain 'a1*' that binds to one end 'a1' (e.g., 5' end) of one of the docking-strand sequences, a central domain that comprises a TT linker, and another end domain 'a.2*' that binds to one end '2a' (e.g., the 3' end) of the other docking strand sequence. As used herein, the terms linker and spacer are used interchangeably. FIG. 1C shows a DNA origami structure that was "labeled" with pPAINT oligos in its four corners: when the pair of pPAINT oligos was present, a DNA-PAINT super-resolution fluorescence image was obtained using Cy3b-labeled imager strands. When only one of the pPAINT oligos was present, no visible trace was obtained. FIG. 1D shows a DNA origami nanostructure containing extensions with the pPAINT probes, demonstrating that the desired geometry can be visualized with the control DNA-PAINT docking sites (P16 and P38) and the pPAINT docking site (pP1). FIG. 1E shows secondary structures adopted by the pair of pPAINT probes (i), motif 2 (ii) and motif 1 (iii). Each motif was designed to adopt a secondary structure that is weak enough to guarantee that when the two probes are in close proximity they adopt the secondary structure depicted in (i), but is strong enough to prevent the formation of multivalent interactions. This last feature is useful, for example, because antibodies are usually labeled with more than one DNA probe, thus multivalent interactions can cause the formation of the pPAINT docking site (i) even when only one of the targets is present.

DETAILED DESCRIPTION

Figure 1C:
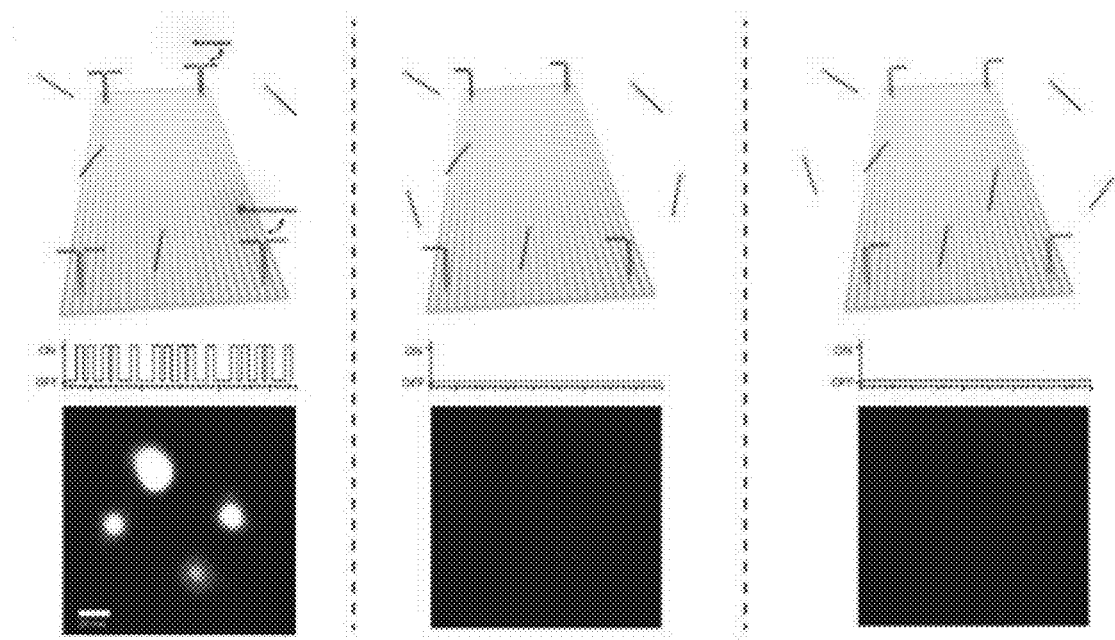
Figure 1D:
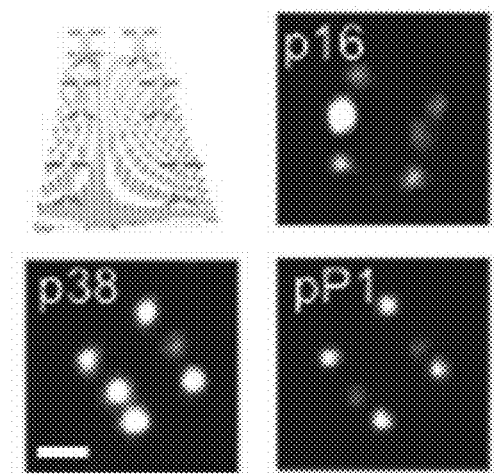
Figure 1E:
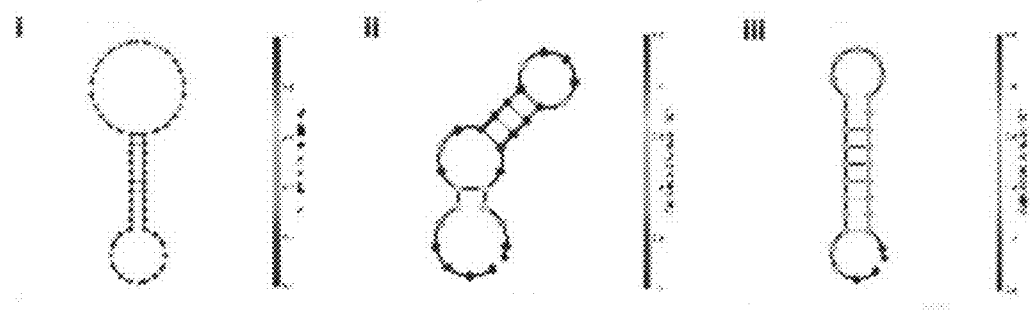

The present disclosure provides a modification to traditional DNA-PAINT methodology. Rather than imaging a single target, such as a single protein or a single nucleic acid, the methods of the present disclosure detect targets (e.g., two targets) that are interacting with each other. The methods yield signal only when a pair of targets are in proximity to each other such that the two targets can be regarded as binding to each other or being complexed to each other. When the targets are not sufficiently close to each other, no signal is detected. The present disclosure therefore provides an unexpected use of the DNA-PAINT methodology, as well as compositions relating to such use.

DNA-PAINT is a super-resolution imaging methodology that involves stochastic, short-lived binding of labeled oligonucleotides to targets that are separated from each other by a distance that is less than a diffraction limited distance. The method relies on the binding of oligonucleotides to only a subset of targets at any given time. The subset of targets may be one or more (e.g., 2, 3, 4, 5, 6, 7, 8, 9 or 10), and in some instances no target may be bound. When less than all the targets are bound to detectable oligonucleotides, signals from individual targets are more easily discerned from each other. This is in contrast to the situation when all the targets are bound to detectable labels, in which case the signals from the multiple targets are not discernable. Thus, targets that are too close to each other can be resolved spatially by detecting signal, each of them in a temporally staggered manner.

In a DNA-PAINT method, a target is detected through the use of a binding partner that binds specifically to the target. The binding partner in turn is conjugated to an oligonucleotide, referred to herein as a 'docking strand'. Detection further requires the use of another oligonucleotide, referred to as an 'imager strand' (probe) that is complementary to the docking strand. The docking strand provides the docking site to which the imager strand binds. The imager strand is detectably labeled, including for example fluorescently labeled. DNA-PAINT requires that the interaction between docking and imager strands be short-lived. This is achieved in a number of ways including for example through the length of the docking and imager strands, through the nucleotide sequence of the docking and imager strands, through the concentration of imager strands, through the number of docking strands per target, through the conditions in which the binding interactions occur, and the like.

Other techniques such as bimolecular fluorescence complementation (Hu, Chinenov, & Kerppola, 2002) enable the localization of these interactions within the cell but require high expression levels of fusion proteins. A different approach, named Proximity Ligation Assay (PLA) (Söderberg, et al., 2006) offers high sensitivity and specificity, but the visual signal that indicative of interactions between proteins is still confined to the diffraction limit, and several enzymatic steps are necessary in order to amplify and detect such signal.

Single Molecule Localization (SML) techniques enable the visualization below the diffraction limit, unveiling a myriad of valuable biological information. Many of these implementations use fluorescent ON and OFF states to temporally decouple the localization of proteins within a diffraction-limited area. Both targeted (e.g. Stimulated Emission Depletion microscopy or STED) (Hell, 1994) and stochastic (Photoactivated Localization Microscopy or PALM, and Stochastic Optical Reconstruction Microscopy or STORM) (Rust, Bates, & Zhuang, 2006) (Betzig, et al., 2006) switching methods have achieved unprecedented spatial resolution, but they require either costly equipment and/or specialized experimental conditions.

In contrast, DNA-PAINT utilizes the programmable capabilities of short detectably labeled oligonucleotides ('imager' strands) that transiently bind to their complementary 'docking' strands, achieving the necessary stochastic ON- and OFF-states for single molecule localization thereby facilitating super-resolution microscopy (Jungmann et al. *Nano Lett.* 2010 November 10; 10(11):4756-61, incorporated herein by reference). DNA-PAINT can achieve highly-multiplexed sub-diffraction images with <10 nm spatial resolution in DNA nanostructures. In addition to this, by coupling DNA oligonucleotides to antibodies, DNA-PAINT can been extended to in situ multiplexed two- and three-dimensional super-resolution imaging.

Techniques that combine the resolving power of SML approaches with other assays are also available. These include the combination of Bimolecular Fluorescence Complementation (BiFC) with PALM for super-resolution imaging of protein-protein interactions (Liu, et al., 2014) and the combination of Förster Resonance Energy Transfer (FRET) with universal-PAINT (uPAINT) (Winckler, et al., 2013). These approaches have provided valuable insights into the role of interacting proteins using sub-diffraction limit resolution. Nonetheless, these methods are dependent upon and, thus, limited by the need to express fusion proteins in very high levels. In addition, these methods are restricted to analyses of target proteins in membranes.

Furthermore, multiplexing for a large number of protein pairs is very challenging using these available techniques.

Proximity PAINT

Like DNA PAINT, proximity DNA-PAINT relies on known kinetics of nucleotide sequences. By adjusting the length and sequence of oligonucleotides pairs, it is possible to achieve a transient binding and unbinding that enables the localization of target molecules, such as complexes, within a diffraction-limited area. See International Publication No. WO 2015/017586, filed Jul. 30, 2014, incorporated herein by reference in its entirety.

A system is provided that comprises, in some embodiments, of a pair of nucleotide sequences that will act as a docking site only when they are in close proximity to each other. When the pair are not in close proximity, any interaction between the imager strand and each sequence alone is not stable enough to be detected (FIGS. 1A-B).

FIGS. 1A-C illustrate the proximity-PAINT (pPAINT) method in the context of two interacting proteins. In FIG. 1A, two target proteins are each labeled with one of a pair of p-PAINT oligonucleotides. If the proteins are interacting, the interaction is visible via DNA-PAINT.

FIG. 1B illustrates the pPAINT oligonucleotides design. The two pPAINT oligonucleotides combine to form the docking site. Additionally, they have a short complementary domain (referred to herein as the stability or stem domain) that will bind the oligonucleotides to each other transiently. This domain has a longer mean bound time than the imager strand binding to the docking site. Thus, when the two oligonucleotides are close enough to each other, the imager strand will bind the docking site with higher probability than if oligonucleotides were not close enough together. When the oligonucleotides are not close enough to each other, no significant DNA-PAINT trace (e.g., fluorescent signal) is obtained.

One embodiment of a pPAINT imager strand is illustrated in FIG. 1B. The illustrated imager strand has three domains: a first domain binds the 5'-end nucleotide sequence of the docking site (i.e., the 5' half-docking site); a second domain binds the 3'-end nucleotide sequence of the docking site (i.e., the 3' half-docking site); and a (optional) linker domain situated between the 5' and 3' domains. When present, the linker may be a nucleic acid or it may be non-nucleic acid. In some embodiments, the linker comprises 1-5 nucleotides. The nucleotides may be A, T, C or G residues or some combination, variant or modified version thereof. The linker may be comprised of abasic sites. It is important that, when present, the linker sequence does not bind to sequence in either of the half-docking sites. Rather the linker functions to separate the 5' and 3' domains from each other sufficiently so that they may bind to their complementary sequences on the half-docking sites. In some embodiments, the linker domain may consist of only T residues, such as T, TT, TTT, TTTT or TTTTT. In some embodiments, the linker domain may consist of only A residues, such as A, AA, AAA, AAAA or AAAAA. In some embodiments, the linker domCin mCy consist of only C residues, such Cs C, CC, CCC, CCCC or CCCCC. In some embodiments, the linker domGin mGy consist of only G residues, such Gs G, GG, GGG, GGGG or GGGGG. Thus, a linker may be, for example, a homopolymers consisting of only A (polyA), T (polyT), C (polyC) or G (polyC).

For in vitro analysis, a DNA origami structure (nanostructure) was "labeled" with pPAINT oligonucleotides in its four corners, as shown schematically in FIG. 1C. When the pair of pPAINT oligonucleotides are present, a DNA-PAINT super-resolution fluorescence image was obtained using Cy3b-labeled imager strands. When only one of the pPAINT oligonucleotides is present, no visible trace was obtained.

The pPAINT oligonucleotides conjugated to target-specific binding partners are designed with short complementary (stem or stability) domains that will bind (hybridize) to each other) transiently. The mean bound time for the stem domains is longer than the mean bound time for the imager—docking site binding. Therefore the stem domain confers a certain degree of stability to the docking site complex in order to increase the probability of imager strand binding. The imager strand binds the 5'-end of the docking site (imparted by one oligonucleotide) and the 3'-end of the docking site (imparted by the other oligonucleotide).

The imager strand illustrated in FIG. 1B comprises the 5' and 3' domains that each bind to a half-docking site, with a linker domain in the middle. The imager may be longer than previously used imager strands. The increased length compensates for the thermodynamic penalty of having a small loop in the middle (FIG. 1B).

The present disclosure provides, inter alia, methods for detecting interactions between various targets, such as interactions between at least two (e.g., 2, 3, 4 or 5) proteins, or interactions between proteins and other moieties.

The methods of the present disclosure can be used to study interactions in cells or in cell lysates. Additionally, they may be used to study interactions between targets in vitro such as part of a screening assay or platform.

Docking Sites, Half-Docking Sites, and Half-Docking Strands

In the methods provided herein, the "docking site" comprises two "half-docking sites," each half site contributed by a target-specific binding partner. Thus, when two targets are complexed with each other, binding partners bound to the two targets will be in close proximity to each other as will the oligonucleotides conjugated to the binding partners. When the oligonucleotides are in close proximity to each other, together they form a full docking site to which an imager strand can hybridize. If the targets are not complexed, then the binding partners are not likely to be located within sufficient proximity of each other, and the oligonucleotides to which they are bound will not interact with each other, and consequently no docking site will be formed.

The system and its components are designed such that imager strands do not bind to either of the half-docking sites for the period of time required to observe such binding. Thus the combination of the two half-docking sites is needed for imager strand binding. Only when the imager strand is bound, a detectable signal coming from the focal plane will be obtained. Unbound imager strands are typically outside of the focal plane and thus not detected, although they can contribute to noise.

The oligonucleotides conjugated to the binding partners each comprise a half-docking site domain, a stability (or stem) domain, optionally a spacer domain between the half-docking site domain and the stability domain, and optionally a spacer domain between the end of the oligonucleotide conjugated to the binding partner and the stability domain. The half-docking site domain is the nucleotide sequence that combines with another half-docking site domain imparted by the oligonucleotide conjugated to another binding partner to form a full docking site to which a complementary imager strand binds. The stability domain is a nucleotide sequence that is complementary to a stability domain in another oligonucleotide conjugated to another binding partner. When two targets are interacting and these oligonucleotides are in sufficiently close proximity, they hybridize to each other through their stability domains to form a double-stranded stem domain. Such hybridization helps to stabilize the full docking site formed by the combination of the two half-docking sites domains. The oligonucleotides may optionally comprise 1 or 2 spacer domains. The spacer domain may facilitate the hybridization of the oligonucleotides to each other and/or hybridization of the imager strand to the docking site.

The oligonucleotide is typically single-stranded although it may comprise double stranded regions prior to binding to another oligonucleotide conjugated to another binding partner.

The present disclosure contemplates that the hybridization between the two oligonucleotides, via their stability domains, will be more stable than the binding of the imager strand to the docking site. The present disclosure further contemplates that the binding of the two complexes to each other will be more stable than the hybridization between the two oligonucleotides. In other words, the free energies of the various interactions are as follows: target-target interaction>oligo-oligo hybridization>imager strand-docking site.

The full docking site may have a length of about 8 nucleotides to about 60 nucleotides, about 8 to about 50 nucleotides, about 8 to about 40 nucleotides, about 8 to about 30 nucleotides, about 8 to about 20 nucleotides, about 8 to about 15 nucleotides, or about 10 to about 14 nucleotides, including a length of 8, 9, 10, 11, 12, 13 or 14 nucleotides. In some embodiments, the full docking site is 8-14 nucleotides in length, or 9-13 nucleotides in length, or 10-12 nucleotides in length. The imager strand length is typically at least the length of the full docking site.

The half-docking site ranges in length from about 4 nucleotides to about 100 nucleotides. In some embodiments, a docking strand is about 4 to about 20 nucleotides, about 4 to about 10 nucleotides, including 4, 5, 6, 7, 8, 9 or 10 nucleotides in length. In some embodiments, a docking strand has a length of 4 to 50, or 4 to 100 nucleotides. For example, a a docking strand may have a length of 4 to 10, 4 to 15, 4 to 20, 4 to 25, 4 to 30, 4 to 35, 4 to 40, 4 to 45, 4 to 50, 4 to 55, 4 to 60, 4 to 60, 4 to 70, or 4 to 75 nucleotides.

The half-docking sites may contribute an equal number of nucleotides to the full docking site, or they may contribute an unequal number of nucleotides to the full docking site. For example, the half-docking sites may each contribute 4, 5, 6, 7 or more nucleotides. In some embodiments, the half-docking sites each contribute 4 or 5 nucleotides. The half-docking sites contribute 5 nucleotides, or 6 nucleotides, or 7 nucleotides.

The stability or stem domains may be about 8 to about 20 nucleotides in length, or about 8 to about 15 nucleotides in length, including 8, 9, 10, 11, 12, 13 or 14 nucleotides in length.

The oligonucleotide may comprise a spacer domain between the stability domain and the half-docking site domain. Such spacer domain may be 1-5 nucleotides in length, for example. The nucleotides may be T residues, or they may be abasic residues. Such spacer domain should not hybridize with the imager strand. In some embodiments, there is no spacer domain between the stability domain and the half-docking site.

The oligonucleotide may comprise a spacer domain between the conjugated end of the oligonucleotide and the stability domain. This spacer domain may be 1-100 nucleotide in length or longer, including for example 5-100 nucleotides in length. The spacer domain may be up to 5, 10, 20, 30, 40, 50, 60, 70, 80, 90 and 100 nucleotides. In some embodiments, the spacer domain is up to or about 40 nm in length, including about 2.5 nm, 5 nm, 10 nm, 15 nm, 20 nm, 30 nm, or longer.

Imager Strands

An "imager strand" is a single-stranded nucleic acid (e.g., DNA) that binds transiently to the docking site. The imager strand may be about the same length as the docking site. Thus, without a linker domain, the imager strand may be about 8 nucleotides to about 50 nucleotides in length, about 8 to about 40 nucleotides, about 8 to about 30 nucleotides, about 8 to about 20 nucleotides, about 8 to about 15 nucleotides, or about 10 to about 14 nucleotides, including 8, 9, 10, 11, 12, 13 or 14 nucleotides in length. In some embodiments, the imager strand is 8-14 nucleotides in length, or 9-13 nucleotides in length, or 10-12 nucleotides in length, in the absence of a linker domain or sequence.

In some embodiments, the imager strand is 14 nucleotides in length, comprising the 5' and 3'domains, each of which is 6 nucleotides in length, and a 2 nucleotide linker.

In some embodiments, the imager strand is 8-20 nucleotides in length, comprising the 5' and 3'domains, each of which is 4-8 nucleotides in length, and a 1-4 nucleotide linker.

An imager strand is complementary to and transiently binds to a full docking site. Two nucleic acids or nucleic acid domains are "complementary" to one another if they base-pair, or bind, with each other to form a double-stranded nucleic acid molecule via Watson-Crick interactions. As used herein, "binding" refers to an association between at least two molecules due to, for example, electrostatic, hydrophobic, ionic and/or hydrogen-bond interactions under physiological conditions. An imager strand is considered to "transiently bind" to a docking site if it binds to a complementary region of a docking site and then disassociates (unbinds) from the docking site within a short period of time. These interactions may occur at room temperature in some embodiments. In some embodiments, an imager strand remains bound to a docking strand for about 0.1 to about 10, or about 0.1 to about 5 seconds. For example, an imager strand may remain bound to a docking strand for about 0.1, about 1, about 5 or about 10 seconds.

In the presence of the linker domain, the imager strand may be at least 1-5 nucleotides longer than the above-recited lengths.

Imager strands of the present disclosure may be labeled with a detectable label (e.g., a fluorescent label, in which case they are considered to be "fluorescently labeled"). For example, in some embodiments, an imager strand may comprise at least one (i.e., one or more) fluorophore. Examples of fluorophores for use in accordance with the present disclosure include, without limitation, xanthene derivatives (e.g., fluorescein, rhodamine, Oregon green, eosin and Texas red), cyanine derivatives (e.g., cyanine, indocarbocyanine, oxacarbocyanine, thiacarbocyanine and merocyanine), naphthalene derivatives (e.g., dansyl and prodan derivatives), coumarin derivatives, oxadiazole derivatives (e.g., pyridyloxazole, nitrobenzoxadiazole and benzoxadiazole), pyrene derivatives (e.g., cascade blue), oxazine derivatives (e.g., Nile red, Nile blue, cresyl violet and oxazine 170), acridine derivatives (e.g., proflavin, acridine orange and acridine yellow), arylmethine derivatives (e.g., auramine, crystal violet and malachite green), and tetrapyrrole derivatives (e.g., porphin, phthalocyanine and bilirubin). Other detectable labels may be used in accordance with the present disclosure, such as, for example, gold nanoparticles or other detectable particles or moieties.

In some embodiments, imager strands are labeled in a target-specific manner. This intends that imager strands that are specific for a complex A are labeled with a spectrally distinct label. As used herein, "spectrally distinct" labels refer to labels (e.g., fluorophores) of different spectral signal or wavelength. For example, an imager strand labeled with a Cy2 fluorophore emits a signal at a wavelength of light of about 510 nm, while an imager strand labeled with a Cy5 fluorophore emits a signal at a wavelength of light of about 670 nm. Thus, the Cy2-labeled imager strand is spectrally distinct from the Cy5-labeled imager strand.

Conversely, "spectrally indistinct" labels are labels having the same spectral signal or wavelength—that is, the emission wavelength of the labels cannot be used to distinguish between two spectrally indistinct fluorescently labels because the wavelengths are the same or close together. In some embodiments, the imager strands are labeled in a non-target specific manner. The imager strands may be labeled with the same labels or with spectrally indistinct labels.

The methods provided herein may be used to detect a plurality of interactions, and in this way the methods may be referred to as multiplexed methods or assays. Different interactions may be distinguished from each other temporally, or through the use of spectrally distinct signals, or through differences in the blinking frequency of the imager strand—docking site interaction. Different targets can be distinguished temporally using different imager strands sequentially and not concurrently. For example, a first imager strand specific for a first interaction is used to detect the presence of the first interaction, and then a second imager strand specific for a second interaction is used to detect the presence of the second interaction, etc. Different imager strands refer to imager strands having different nucleotide sequence that detect different docking sites. Different targets can be distinguished spectrally using different imager strands that are labeled with spectrally distinct labels. For example, a first imager strand having a Cy2 label is used to detect a first interaction and a second imager strand having a Cy5 label is used to detect a second interaction. These spectrally distinct imager strands can be used concurrently. Different targets can be distinguished by imager strand—docking site combinations having different blinking frequencies. As described herein, the blinking frequency of an imager strand—docking site interaction can be modulated in order to have a defined and distinct ON and/or OFF rates. In this way, some imager strands—docking site pairs may bind and unbind at higher frequency and thereby appear to "blink" more frequently than other pairs. In this way, the imager strands may be labeled with spectrally indistinct labels, including with the same labels, and yet still used at the same time because their blinking frequencies are different. Blinking frequency can be modulated by changes in imager strand length and correspondingly docking sites, altering the sequence composition (e.g., more AT rich or more GC rich), altering melting temperatures using other methods including for example altering the hybridization conditions, altering the number of docking sites per target, increasing the concentration of imager strands, etc.

Binding Partners

The method can be used to detect the interaction of virtually any moieties for which binding partners exist or can be made provided such binding partners can be conjugated to an oligonucleotide.

Binding partners conjugated to an oligonucleotide may be referred to here as binding partner-nucleic acid (BP-NA) conjugates or binding partner-oligonucleotide (BP-Oligo) conjugates. As used herein, BP-NA or BP-Oligo conjugates refer to a molecule linked (e.g., through an N-Hydroxysuccinimide (NHS) linker) to a single-stranded nucleic acid (e.g., DNA). The single-stranded nucleic acid comprises a half-docking site, a stability domain and optionally a spacer domain.

The binding partners may be any moiety (e.g., antibody or aptamer) that has an affinity for (e.g., binds to) a target, such as a biomolecule (e.g., protein or nucleic acid), of interest. In some embodiments, the binding partner is a protein. Examples of proteins for use in the conjugates of the present disclosure include, without limitation, antibodies (e.g., monoclonal antibodies), antigen-binding antibody fragments (e.g., Fab fragments), receptors, peptides and peptide aptamers. Other binding partners may be used in accordance with the present disclosure. For example, binding partners that bind to targets through electrostatic (e.g., electrostatic particles), hydrophobic or magnetic (e.g., magnetic particles) interactions are contemplated herein.

As used herein, "antibody" includes full-length antibodies and any antigen binding fragment (e.g., "antigen-binding portion") or single chain thereof. The term "antibody" includes, without limitation, a glycoprotein comprising at least two heavy (H) chains and two light (L) chains interconnected by disulfide bonds, or an antigen binding portion thereof. Antibodies may be polyclonal or monoclonal; xenogeneic, allogeneic, or syngeneic; or modified forms thereof (e.g., humanized, chimeric).

As used herein, "antigen-binding portion" of an antibody, refers to one or more fragments of an antibody that retain the ability to specifically bind to an antigen. The antigen-binding function of an antibody can be performed by fragments of a full-length antibody. Examples of binding fragments encompassed within the term "antigen-binding portion" of an antibody include (i) a Fab fragment, a monovalent fragment consisting of the VH, VL, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VH and VL domains of a single arm of an antibody, (v) a dAb fragment (Ward et al., *Nature* 341:544 546, 1989), which consists of a VH domain; and (vi) an isolated complementarity determining region (CDR) or (vii) a combination of two or more isolated CDRs, which may optionally be joined by a synthetic linker. Furthermore, although the two domains of the Fv fragment, VH and VL, are coded for by separate genes, they can be joined, using recombinant methods, by a synthetic linker that enables them to be made as a single protein chain in which the VH and VL regions pair to form monovalent molecules (known as single chain Fv (scFv); see, e.g., Bird et al. *Science* 242:423 426, 1988; and Huston et al. *Proc. Natl. Acad. Sci. USA* 85:5879-5883, 1988). Such single chain antibodies are also encompassed within the term "antigen-binding portion" of an antibody. These antibody fragments are obtained using conventional techniques known to those with skill in the art, and the fragments are screened for utility in the same manner as are intact antibodies.

As used herein, "receptors" refer to cellular-derived molecules (e.g., proteins) that bind to ligands such as, for example, peptides or small molecules (e.g., low molecular weight (<900 Daltons) organic or inorganic compounds).

As used herein, "peptide aptamer" refers to a molecule with a variable peptide sequence inserted into a constant scaffold protein (see, e.g., Baines I C, et al. *Drug Discov. Today* 11:334-341, 2006). In some embodiments, the molecule of the BP-NA conjugate is a nucleic acid such as, for example, a nucleic acid aptamer. As used herein, "nucleic acid aptamer" refers to a small RNA or DNA molecules that can form secondary and tertiary structures capable of specifically binding proteins or other cellular targets (see, e.g., Ni X, et al. *Curr Med Chem.* 18(27): 4206-4214, 2011). Thus, in some embodiments, the BP-NA conjugate may be an aptamer-nucleic acid conjugate.

In an important embodiments, the binding partner is an antibody or an antigen-binding antibody fragment that binds to the target of interest.

Targets

A target may be any molecule of interest or any binding site on a molecule (e.g., biomolecule) of interest. Examples of targets include, but are not limited to, proteins and nucleic acids (DNA and/or RNA, such as mRNA). Examples of proteins include, but are not limited to, enzymes, proteins involved in cell signaling, ligand binding and/or localization, as well as structural proteins. In some embodiments, the target is an epitope of a protein.

A pair of targets may be a pair if the same type of molecule or a pair of different types of molecules. For example, a pair of targets may include Protein A and Nucleic Acid A, Protein A and Protein B, or Nucleic Acid A and Nucleic Acid B.

Methods

Also provided herein are methods of detecting a (at least one) complex of two targets in a sample, the method comprising contacting a sample with the imager strand of any one of paragraphs 29-44 and the binding partner-oligonucleotide conjugates of any one of paragraphs 29-44, wherein the binding partner of (a) has specificity for one of the two targets, and the binding partner of (b) has specificity for the other of the two targets; and detecting presence or absence of the complex in the sample.

A sample may be a biological sample, such as a tissue sample, including a blood (e.g., serum and/or plasma) sample, cerebrospinal fluid sample, urine sample, or other biological sample. In some embodiments, the sample is a cell or cell lysate. The cell may be a mammalian cell, a bacterial cell, a yeast cell or an insect cell, for example. Other cells and lysates of cells are encompassed herein.

A target, in some embodiments, is a biomolecule, such as a protein or a nucleic acid. Examples of proteins of interest include, but are not limited to, enzymes, proteins involved in cell signaling, ligand binding and/or localization, as well as structural proteins. Examples of nucleic acids include, but are not limited to, DNA and RNA (e.g., mRNA), naturally occurring or engineered (e.g., synthetic or recombinant).

In some embodiments, target complexes are located within a sub-diffraction distance of each other. That is, when using an optical imaging system—e.g., a microscope—the resolution of interacting targets is diffraction limited (there is a fundamental maximum to the resolution of any optical system which is due to diffraction).

The conditions under which a method is performed can be determined by one of ordinary skill in the art with an understanding of nucleic acid hybridization kinetics. Such conditions may be varied. For example, methods are of target detection may be performed in reaction buffer or cell lysate having a particular concentration of salt, as needed, and any other necessary reagents to permit nucleic acid hybridization and 'blinking' kinetics (as discussed above).

Kits

Also provided herein are kits. Kits may include, for example, binding partner-oligonucleotide conjugate pairs, either as individual components (binding partner and oligonucleotide separately) or as a conjugate (binding partner linked to oligonucleotide) as well as imager strands, with or without labels, as provided herein. Any component (e.g., binding partner, nucleic acid, linker, etc.) that may be included in a composition, as provided herein, may also be included in a kit where, for example, individual components are packaged (e.g., in separate storage containers) and provided together in a larger package (e.g., box).

The present disclosure further provides embodiments encompassed by the following numbered paragraphs:

1. A kit, system or composition comprising
    a first binding partner-oligonucleotide conjugate comprising a first binding partner linked to a first oligonucleotide, wherein the first oligonucleotide comprises a first half-docking domain, a first stability domain, and optionally a first spacer domain,
    a second binding partner-oligonucleotide conjugate comprising a second binding partner linked to a second oligonucleotide, wherein the second oligonucleotide comprises a second half-docking domain, a second stability domain, and optionally a second spacer domain, wherein the first and second stability domains are complementary to each other, and wherein the first and second half-docking domains combine linearly to form a full docking domain, and
    an imager strand comprising a 5' domain and a 3' domain and a linker domain between the 5' domain and the 3' domain, wherein the 5' domain is complementary to the first half-docking domain and the 3' domain is complementary to the second half-docking domain.

2. The kit, system or composition of paragraph 1, wherein the first and second binding partners are antibodies or antigen-binding antibody fragments.

3. The kit, system or composition of paragraph 1 or 2, wherein the first and second binding partners bind to first and second proteins, wherein the first and second proteins are different from each other.

4. The kit, system or composition of any one of paragraphs 1-3, wherein the first and second half-docking domains are 5-7 nucleotides in length.

5. The kit, system or composition of any one of paragraphs 1-4, wherein the first and second half-docking domains are both 6 nucleotides in length.

6. The kit, system or composition of any one of paragraphs 1-5, wherein the first and second stability domains are 9-11 nucleotides in length.

7. The kit, system or composition of any one of paragraphs 1-6, wherein the imager strand is 10-12 nucleotides in length or 12-14 nucleotides in length.

8. The kit, system or composition of any one of paragraphs 1-7, wherein the 5' and 3' domains are 6 nucleotides in length.

9. The kit, system or composition of any one of paragraphs 1-8, wherein the linker domain is 1-5 nucleotides in length.

10. The kit, system or composition of any one of paragraphs 1-9, wherein the linker domain comprises T residues.

11. The kit, system or composition of any one of paragraphs 1-10, wherein the linker domain comprises a TT sequence.

12. The kit, system or composition of any one of paragraphs 1-11, wherein the imager strand is detectably labeled.

13. The kit, system or composition of any one of paragraphs 1-12, wherein the imager strand is fluorescently labeled.

14. The kit, system or composition of any one of paragraphs 1-13, wherein the binding partner is conjugated to the oligonucleotide via streptavidin and biotin.

15. The kit, system or composition of any one of paragraphs 1-14, further comprising a complex comprising a first and a second target, wherein the first binding partner binds or is bound to the first target and the second binding partner binds or is bound to the second target.

16. The kit, system or composition of paragraph 15, wherein the first and second targets are proteins.

17. A plurality of the kit, system or composition of any one of paragraphs 1-16, wherein the imager strands of different systems are labeled with spectrally distinct labels.

18. A plurality of the kit, system or composition of any one of paragraphs 1-16, wherein the imager strands of the different systems are labeled with spectrally indistinct labels.

19. A plurality of the kit, system or composition of any one of paragraphs 1-16, wherein at least one of the systems has a blinking frequency that is distinct from other systems in the plurality.

20. A method of detecting a complex of a first and second target in a sample, the method comprising:
 contacting a sample with
  (a) the first and second binding partner-oligonucleotide conjugates of any one of paragraphs 1-16 wherein the first binding partner has specificity for the first target and the second binding partner has specificity for the second target, and
  (b) the imager strand of any one of paragraphs 1-16; and
 detecting presence of the complex of the first and second target in the sample.

21. The method of paragraph 20, wherein the sample is a cell or cell lysate.

22. The method of paragraph 20 or 21, wherein the first and/or the second target is a protein 23. The method of any one of paragraphs 20-22, wherein the target is obtained from a cell or cell lysate.

24. The method of any one of paragraphs 20-23, wherein the method detects a plurality of complexes.

25. The method of paragraph 24, wherein the plurality of complexes is a plurality of identical complexes.

26. The method of paragraph 24, wherein the plurality of complexes is a plurality of different complexes.

27. The method of any one of paragraphs 24-26, wherein a subset of complexes within the plurality is located within a sub-diffraction distance of each other.

28. A kit, system or composition comprising
 a first binding partner-oligonucleotide conjugate comprising a first binding partner linked to a first oligonucleotide, wherein the first oligonucleotide comprises a first half-docking domain, a first stability domain, and optionally a first spacer domain,
 a second binding partner-oligonucleotide conjugate comprising a second binding partner linked to a second oligonucleotide, wherein the second oligonucleotide comprises a second half-docking domain, a second stability domain, and optionally a second spacer domain, wherein the first and second stability domains are complementary to each other, and wherein the first and second half-docking domains combine linearly to form a first full docking domain,
 a third binding partner-oligonucleotide conjugate comprising a third binding partner linked to a third oligonucleotide, wherein the third oligonucleotide comprises a third half-docking domain, a third stability domain, and optionally a third spacer domain, wherein the first and third stability domains are complementary to each other, and wherein the first and third half-docking domains combine linearly to form a second full docking domain,
 a first imager strand comprising a first 5' domain and a first 3' domain and a first linker domain between the first 5' domain and the first 3'domain, wherein the first 5' domain is complementary to the first half-docking domain and the 3' domain is complementary to the second half-docking domain, and
 a second imager strand comprising a second 5' domain and a second 3' domain and a second linker domain between the second 5' domain and the second 3'domain, wherein the second 5' domain is complementary to the first half-docking domain and the second 3' domain is complementary to the third half-docking domain.

29. A composition comprising:
 (a) a first binding partner-oligonucleotide conjugate comprising a binding partner linked to an oligonucleotide that comprises a half-docking domain, a stability domain, and optionally a spacer domain;
 (b) a second binding partner-oligonucleotide conjugate comprising a binding partner linked to an oligonucleotide that comprises a half-docking domain, a stability domain, and optionally a spacer domain;
 wherein the stability domains of (a) and (b) are complementary to each other, and wherein the half-docking domains of (a) and (b) combine linearly to form a full docking domain; and
 (c) an imager strand comprising a 5' domain, a 3' domain, and a linker domain located between the 5' domain and the 3'domain, wherein the 5' domain is complementary to the half-docking domain of (a) and the 3' domain is complementary to the half-docking domain of (b).

30. The composition of paragraph 29, wherein each of the binding partners of (a) and (b) is an antibody or antigen-binding antibody fragment.

31. The composition of paragraph 29 or 30, wherein each of the binding partners of (a) and (b) binds to a different protein.

32. The composition of any one of paragraphs 29-31, wherein each of the half-docking domains of (a) and (b) has a length of 5-15 nucleotides.

33. The composition of paragraph 32, wherein each of the half-docking domains of (a) and (b) has a length of 5-10 nucleotides.

34. The composition of any one of paragraphs 29-33, wherein each of the stability domains of (a) and (b) has a length of is 5-50 nucleotides.

35. The composition of paragraph 34, wherein the imager strand has a length of 10-30 nucleotides.

36. The composition of any one of paragraphs 29-35, wherein each of the 5' domain and 3' domain of the imager strand has a length of 5-10 nucleotides.

37. The composition of any one of paragraphs 29-36, wherein the linker domain has a length of 1-5 nucleotides.

38. The composition of any one of paragraphs 29-37, wherein the linker domain comprises thymine (T) nucleotides.

39. The composition of any one of paragraphs 29-38, wherein the linker domain comprises a TT sequence.

40. The composition of any one of paragraphs 29-39, wherein the imager strand is detectably labeled.

41. The composition of any one of paragraphs 29-39, wherein the imager strand is fluorescently labeled.

42. The composition of any one of paragraphs 29-41, wherein each of the binding partners of (a) and (b) is respectively conjugated to the oligonucleotide of (a) and (b) via a streptavidin-biotin binding pair.

43. The composition of any one of paragraphs 29-42, further comprising a complex that comprises two targets, wherein the binding partner of (a) binds or is bound to one of the two targets, and the binding partner of (b) binds or is bound to the other of the two targets.

44. The composition of paragraph 43, wherein each of the two targets is a protein.

45. A plurality of the composition of any one of paragraphs 29-44, wherein the imager strands of different compositions within the plurality comprise spectrally-distinct labels.

46. A plurality of any one of paragraphs 29-44, wherein the imager strands of different compositions within the plurality comprise spectrally-indistinct labels.

47. A plurality of any one of paragraphs 29-44, wherein at least one of the compositions of the plurality has a blinking frequency that is distinct from other compositions in the plurality.

48. A method of detecting a complex of two targets in a sample, the method comprising:
contacting a sample with the imager strand of any one of paragraphs 29-44 and the binding partner-oligonucleotide conjugates of any one of paragraphs 29-44, wherein the binding partner of (a) has specificity for one of the two targets, and the binding partner of (b) has specificity for the other of the two targets; and
detecting presence or absence of the complex in the sample.

49. The method of paragraph 48, wherein the sample is a cell or cell lysate.

50. The method of paragraph 48 or 49, wherein each of the two targets is a protein 51. The method of paragraph 50, wherein each of the two targets is obtained from a cell or cell lysate.

52. The method of any one of paragraphs 48-51, further comprising detecting a plurality of complexes of two targets in the sample.

53. The method of any one of paragraphs 48-52, wherein the plurality of complexes is a plurality of different complexes.

54. The method of any one of paragraphs 48-53, wherein a subset of complexes within the plurality is located within a sub-diffraction distance of each other.

55. A method of detecting an intramolecular interaction in a sample, the method comprising:
contacting a sample that comprises a target molecule with
(a) a first binding partner-oligonucleotide conjugate comprising a binding partner linked to an oligonucleotide that comprises a half-docking domain, a stability domain, and optionally a spacer domain, wherein the binding partner of (a) has specificity for one location on a target molecule,
(b) a second binding partner-oligonucleotide conjugate comprising a binding partner linked to an oligonucleotide that comprises a half-docking domain, a stability domain, and optionally a spacer domain, wherein the binding partner of (b) has specificity for another location on the target molecule, wherein the stability domains of (a) and (b) are complementary to each other, and wherein the half-docking domains of (a) and (b) combine linearly to form a full docking domain, and
(c) a imager strand comprising a detectable label, a 5' domain, a 3' domain, and a linker domain located between the 5' domain and the 3'domain, wherein the 5' domain is complementary to the half-docking domain of (a) and
the 3' domain is complementary to the half-docking domain of (b); and detecting presence or absence of the detectable label of the imager strand of (c) in the sample.

56. The method of paragraph 27, wherein the sample is a cell or cell lysate.

57. The method of paragraph 55 or 55, wherein the target molecule is a protein.

58. The method of paragraph 57, wherein each of the location of (a) and (b) is a different epitope on the protein.

59. A composition comprising
(a) a first binding partner-oligonucleotide conjugate comprising a binding partner linked to an oligonucleotide that comprises a half-docking domain, a stability domain, and optionally a spacer domain;
(b) a second binding partner-oligonucleotide conjugate comprising a binding partner linked to an oligonucleotide that comprises a half-docking domain, a stability domain, and optionally a spacer domain;
wherein the stability domains of (a) and (b) are complementary to each other, and wherein the half-docking domains of (a) and (b) combine linearly to form a first full docking domain;
(c) a third binding partner-oligonucleotide conjugate comprising a binding partner linked to an oligonucleotide that comprises a half-docking domain, a stability domain, and optionally a spacer domain,
wherein the stability domains of (a) and (c) are complementary to each other, and wherein the half-docking domains of (a) and (c) combine linearly to form a second full docking domain;
(d) an first imager strand comprising a 5' domain, a 3' domain, and a linker domain located between the 5' domain and the 3'domain, wherein the 5' domain of the first imager strand is complementary to the half-docking domain of (a) and the 3' domain of the first imager strand is complementary to the half-docking domain of (b); and
(e) a second imager strand comprising a 5' domain, a 3' domain, and a linker domain located between the 5' domain and the 3'domain, wherein the 5' domain of the second imager strand is complementary to the half-docking domain of (a) and the 3' domain of the second imager strand is complementary to the half-docking domain of (c).

EXAMPLES

Example 1

Figure 2:
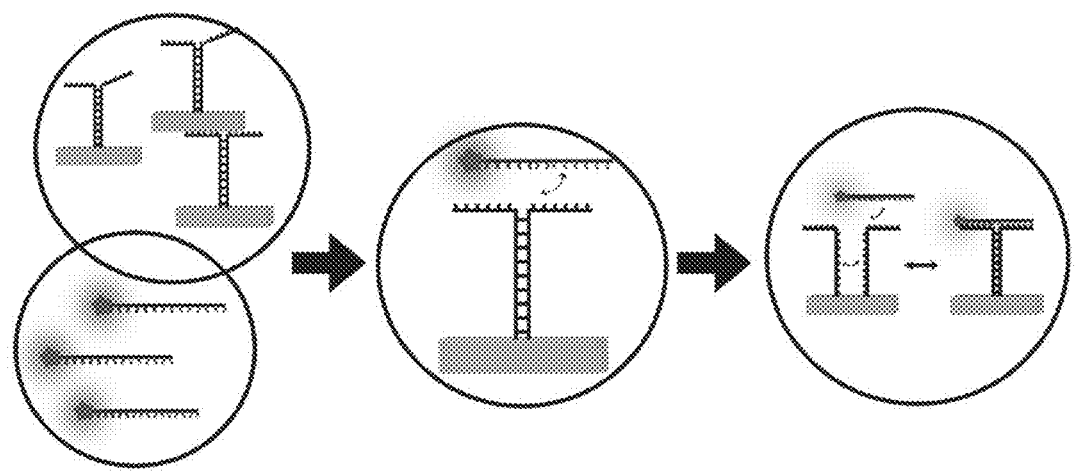
FIG. 2. First stages of pPAINT. (Left panel) Three types of docking sites: TT, T and no spacer in the edge between the stem and one of the docking sites were evaluated with three types of imagers: TTTT, TTT and TT linker in the middle. (Middle panel) The best performing imager with its docking site is chosen based on the kinetic analysis. (Right panel) This pair is used to determine the optimal stem length within a pool of stem designs that ranged from 9-11 bp in length, as an example.

In this Example, the length and design of the linker was analyzed. Linkers consisting of 2, 3 or 4 thymine (T) residues were compared to each other. In addition to this, a short spacer of 1 or 2 T residues was introduced into one of the pPAINT oligonucleotides between the half-docking site domain and the stem (or stability) domain. These different imager strands and oligonucleotides are illustrated in FIG. 2A. Three types of docking sites: TT, T and no spacer between the stem domain and one half-docking domain (in green) were evaluated with three types of imagers: TTTT, TTT and TT linker in the middle (in orange). These combinations were analyzed for their characteristic kinetic parameters. The best performing imager strand with its docking site was chosen based on the kinetic analysis, as represented by FIG. 2B. This pair was used to determine the optimal stem length within a pool of stem designs that ranged from 9-11 bp in length, as illustrated in FIG. 2C.

Figure 3:
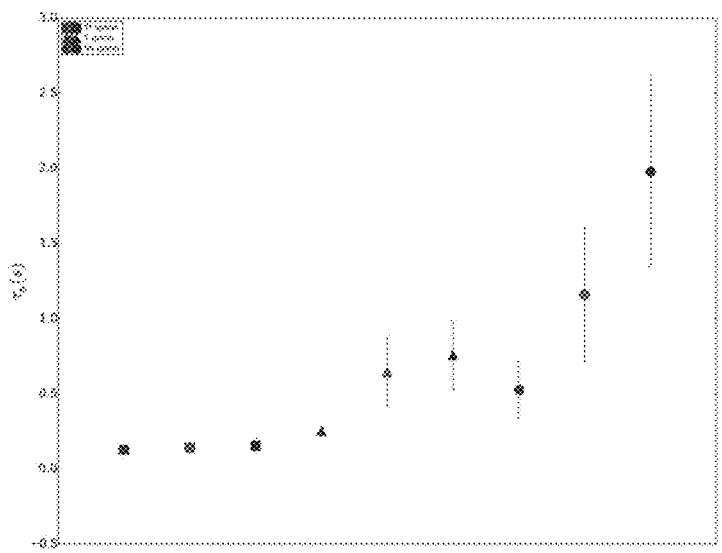
FIG. 3. Mean bound time for three types of docking sites: TT spacer (squares), T spacer (triangles) and no spacer (circles) between the stem and one of the docking site sequences, and the three types of imagers: TTTT (medium gray), TTT (light gray) and TT (dark gray) linker in the middle. In some instances, the design for pPAINT corresponds to the one lacking a spacer at the edge of the stem, and a TT linker in the imager strand.
Figure 4:
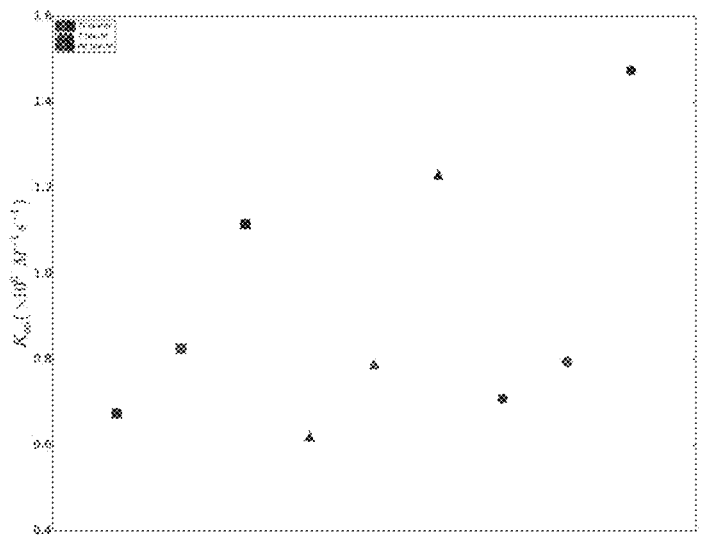
FIG. 4. $K_{on}$ for the three types of docking sites: TT spacer (squares), T spacer (triangles) and no spacer (circles) between the stem and one of the docking site sequences, and the three types of imagers: TTTT (medium gray), TTT (light gray) TT (dark gray) linker in the middle.
Figure 5:
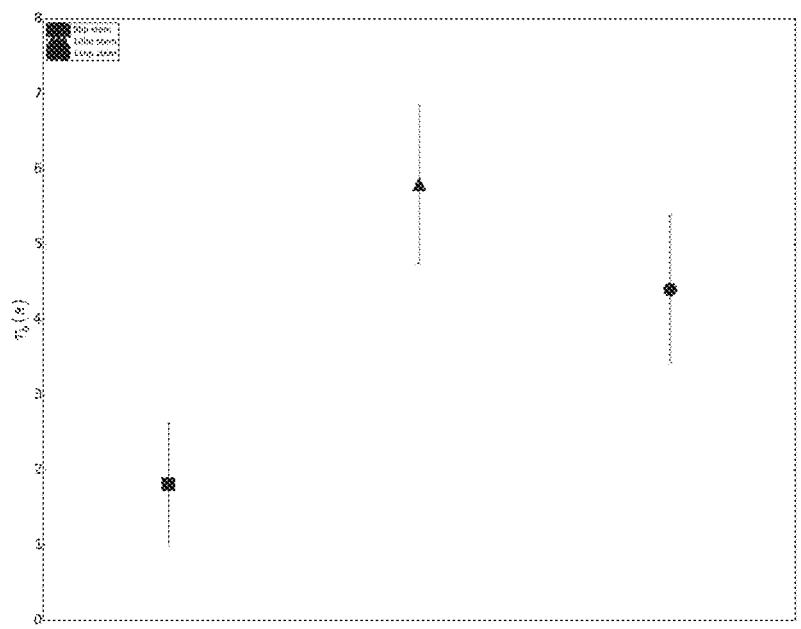
FIG. 5. Mean bound times for the best design per stem length evaluated: S9V2 (square), S10V2 (triangle), S11V1 (circle).
Figure 6:
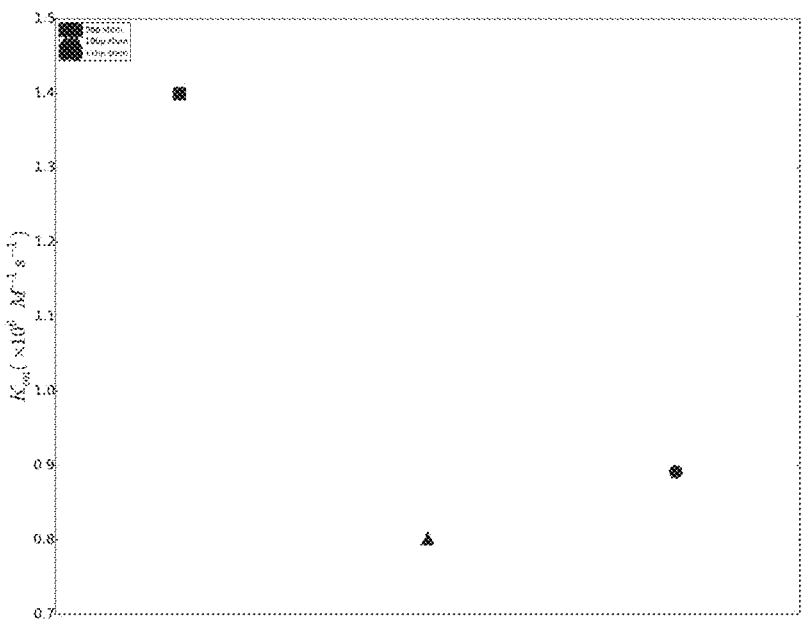
FIG. 6. $K_{on}$ for an example design per stem length evaluated: S9V2 (square), S10V2 (triangle), S11V1 (circle).

In another experiment, the length of the stem domain that holds together the pPAINT oligonucleotides prior to the binding of the imager strand was initially determined by trying out 9, 10 and 11 bp stem domains (Table 1 lists example sequences per length) with both strands located at a distance of 0.35 nm between each other in each of the experiments. From these results, we concluded that the imager strand with a TT linker in between the 5' and 3' domains and the docking site with no spacer performed best with the longest mean bound time and largest Kon as shown in FIGS. 3 and 4. From these results we concluded that the best stem domains were the 11 and 10 bp long, as shown in FIGS. 5 and 6. Both lengths should render a stem domain that will bind transiently, but long enough to enable the imager strand to bind to the docking site.

TABLE 1

Sequences of the stem domains that were tested during the optimization.

| Name of the stem | Sequence |
|---|---|
| S9V2 | 5'-GATGACATC-3' (SEQ ID NO: 1) |
| S10V2 | 5'-TAATAAGGAT-3' (SEQ ID NO: 2) |
| S11V1 | 5'-CTAACTAATTA-3' (SEQ ID NO: 3) |

Figure 7:
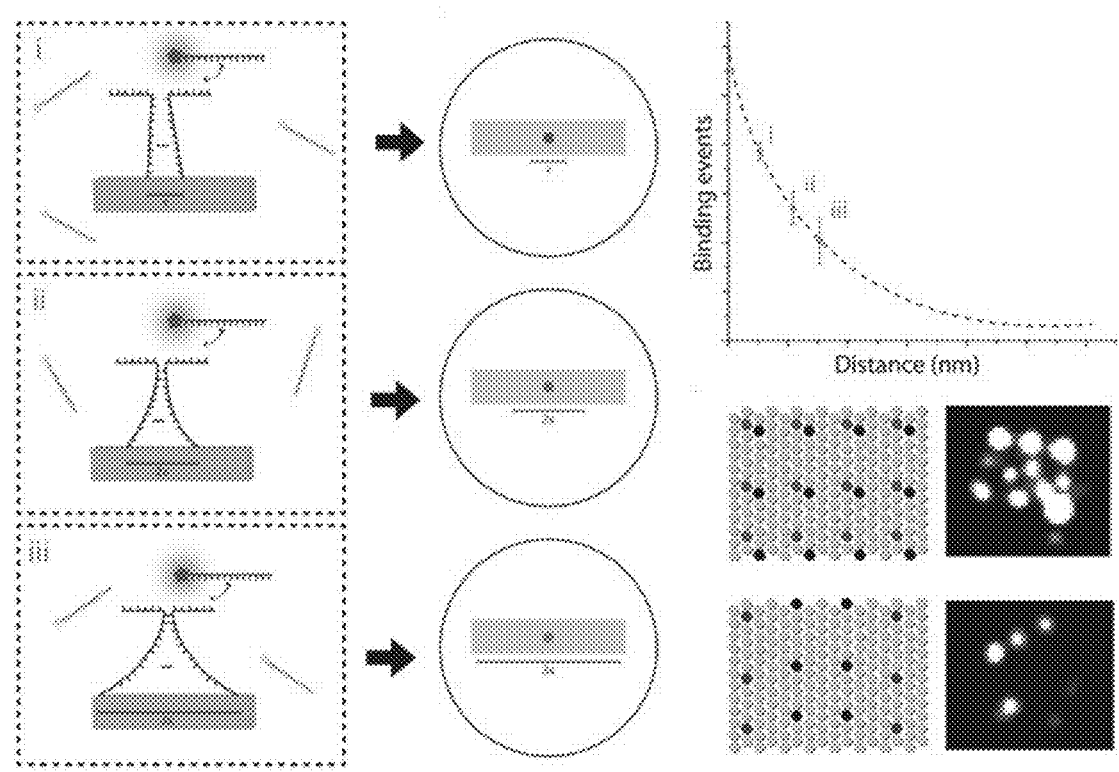
FIG. 7. Detection range for pPAINT. (Left panel) A DNA origami polymer is "labeled" with pPAINT oligos at three different distances. (Middle panel) With increasing distance we expect to see a dimmer signal. (Top right panel) With this characterization, it will be possible to determine the working range for p-PAINT. (Bottom right panel) Preliminary results of the tests performed with the two docking sites at a larger distance. The two pPAINT oligonucleotides were placed at a distance of 5 nm (upper panel) and 20 nm (lower panel) between them. At the left of each panel, the hex-staple representation, where each hexagon represents a staple color-coded for the modification in the 3'-end extension (dark grey) and the 5'-end (black), depicts the position where the two half-docking sites were placed in the DNA origami. With this characterization, it is possible to conclude that the working range of pPAINT is at least 20 nm.

After choosing sequences for the imager and the two half-docking sites, these were tested in DNA origami structures again with a distance of 5 and 20 nm between each other. As shown in FIG. 7, a DNA-PAINT signal was obtained, thus demonstrating that the working range of pPAINT is at least 20 nm, in this example.

Example 2

Figure 8:
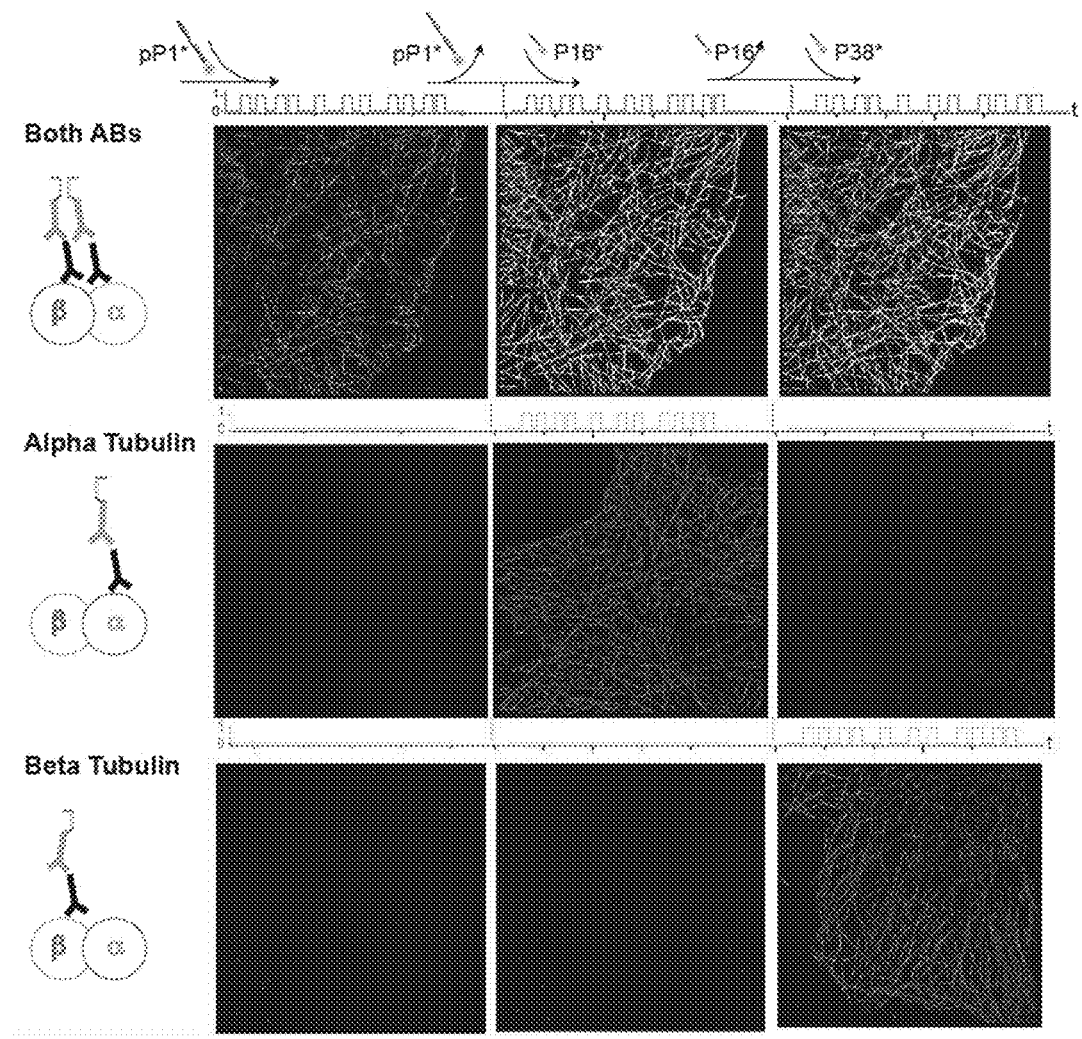
FIG. 8. Benchmarking pPAINT in situ.

This Example describes a benchmarking pPAINT in situ experiment. Alpha and Beta tubulin were selected as the two targets. The positive control (top three panels) included use of primary antibodies against alpha and beta tubulin and secondary antibodies against each of their primary antibody targets, each labeled with one of the pPAINT motifs (FIG. 8). Microtubules were visible when imaging with pP1, P16 and P38. The negative controls included adding only one of the primary antibodies and both secondary antibodies. For the first one, only anti alpha tubulin was added (middle three panels) thus microtubules were visible when using only P16. For the second negative control, only anti beta tubulin was added and microtubules were observed only when using P38. With the embodiments described in FIGS. 1A-1E, pPAINT can be used to detect protein interactions by using traditional immunolabeling techniques that require only PBS, for example, to wash away the excess oligo-labeled antibodies.

Range of distance between the probes: up to 10 nm
pP1.motif1.10nm:
(SEQ ID NO: 4)
ATACAACGAACTATTCGTTAGTTTGTTT pP1.motif2.10nm:
(SEQ ID NO: 5)
TATTTAGTGTTCGAATAGTTCGATCTAG Range of distance between the probes: up to 15 nm
pP1.motif1.15nm:
(SEQ ID NO: 6)
ATA CAA CGA ACT ATT CGT TAG TTT GTT TTT TT pP1.motif2.15nm:
(SEQ ID NO: 7)
TT TTT ATT TAG TGT TCG AAT AGT TCG ATC TAG

REFERENCES

Betzig, E., Patterson, G., Sougrat, R., Lindwasser, O., Olenych, S., Bonifacino, J., et al. (2006). Imaging intracellular fluorescent proteins at nanometer resolution. *Science*, 313, 1642-5.

Hell, S. &. (1994). Breaking the diffraction resolution limit by stimulated emission: stimulated-emission-depletion fluorescence microscopy. *Opt Lett*, 19, 780-2.

Hu, C., Chinenov, Y., & Kerppola, T. (2002). Visualization of interactions among bZIP and Rel family proteins in living cells using bimolecular fluorescence complementation. *Molecular Cell*, 9, 789-798.

Jungmann, R., Steinhauer, C., Scheible, M., Kuzyk, A., & Tinnefeld, P. &. (2010). Single-Molecule Kinetics and Super-Resolution Microscopy by Fluorescence Imaging of Transient Binding on DNA Origami. *Nano Letters*, 10, 4756-4761.

Liu, Z., Xing, D., Su, Q. P., Zhu, Y., Zhang, J., Kong, X., et al. (2014). Super-resolution imaging and tracking of protein-protein interactions in sub-diffraction cellular space. *Nature Communications*, 5.

Rust, M. J., Bates, M., & Zhuang, X. (2006). Sub-diffraction-limit imaging by stochastic optical reconstruction microscopy (STORM). *Nature methods*, 3, 793-5.

Soderberg, O., Gullberg, M., Jarvius, M., Ridderstrale, K., Leuchowius, K., Jarvius, J., et al. (2006). Direct observation of individual endogenous protein complexes in situ by proximity ligation. *Nature methods*, 3, 995-1000.

Winckler, P., Lartigue, L., Giannone, G., De Giorgi, F., Ichas, F., Sibarita, J.-B., et al. (2013). Identification and super-resolution imaging of ligand-activated receptor dimers in live cells. *Scientific Reports*, 3.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of detecting an intermolecular interaction between a first target molecule and a second target molecule, the method comprising:
 (a) contacting a sample comprising the first target molecule and the second target molecule with:
  (i) a first conjugate comprising a first binding partner linked to a first oligonucleotide that comprises a first half-docking domain and a stability domain, wherein the first binding partner binds to the first target molecule in the sample,
  (ii) a second conjugate comprising a second binding partner linked to a second oligonucleotide that comprises a second half-docking domain and a stability domain, wherein the second binding partner binds to the second target molecule in the sample, and wherein the stability domain of the first conjugate binds to the stability domain of the second conjugate, thereby bringing together the half-docking domains to form a full docking domain, and
  (iii) a detectably-labeled imager strand that binds to the full docking domain, wherein the imager strand is detectable only when bound to the full docking domain; and
 (b) detecting the detectably-labeled imager strand bound to the full docking domain, thereby detecting the intermolecular interaction between the first target molecule and the second target molecule in the sample.

2. The method of claim 1, wherein the first binding partner and the second binding partner are antibodies.

3. The method of claim 1, wherein the first binding partner and the second binding partner are antigen-binding antibody fragments.

4. The method of claim 1, wherein the first target molecule and the second target molecule are proteins.

5. The method of claim 1, wherein the detectably-labeled imager strand comprises a fluorescent label.

6. The method of claim 1, wherein the first binding partner is linked to the first oligonucleotide via a streptavidin-biotin binding pair, and the second binding partner is linked to the second oligonucleotide via a streptavidin-biotin binding pair.

7. The method of claim 1, wherein the first oligonucleotide comprises a spacer domain between the half-docking domain and the stability domain, and the second oligonucleotide comprises a spacer domain between the half-docking domain and the stability domain.

8. The method of claim 1, wherein the half-docking domain of the first conjugate has a length of 5-15 nucleotides, and the half-docking domain of the second conjugate has a length of 5-15 nucleotides.

9. The method of claim 1, wherein the stability domain of the first conjugate has a length of 5-50 nucleotides, and the stability domain of the second conjugate has a length of 5-50 nucleotides.

10. The method of claim 1, wherein the detectably-labeled imager strand has a length of 10-30 nucleotides.

11. A method of detecting an intramolecular interaction on a target molecule, the method comprising:
 (a) contacting a sample comprising the target molecule with:
  (i) a first conjugate comprising a first binding partner linked to a first oligonucleotide that comprises a first half-docking domain and a stability domain, wherein the first binding partner binds to a first binding site on the target molecule in the sample,
  (ii) a second conjugate comprising a second binding partner linked to a second oligonucleotide that comprises a second half-docking domain and a stability domain,
  wherein the second binding partner binds to a second target site on the target molecule in the sample, and
  wherein the stability domain of the first conjugate binds to the stability domain of the second conjugate, thereby bringing together the half-docking domains to form a full docking domain, and
  (iii) a detectably-labeled imager strand that binds to the full docking domain, wherein the imager strand is detectable only when bound to the full docking domain; and
 (b) detecting the detectably-labeled imager strand bound to the full docking domain, thereby detecting an intramolecular interaction on the target molecule in the sample.

12. The method of claim 11, wherein the first binding partner and the second binding partner are antibodies.

13. The method of claim 11, wherein the first binding partner and the second binding partner are antigen-binding antibody fragments.

14. The method of claim 11, wherein the first binding site and the second binding site are epitopes.

15. The method of claim 11, wherein the detectably-labeled imager strand comprises a fluorescent label.

16. The method of claim 11, wherein the first binding partner is linked to the first oligonucleotide via a streptavidin-biotin binding pair, and the second binding partner is linked to the second oligonucleotide via a streptavidin-biotin binding pair.

17. The method of claim 11, wherein the first oligonucleotide comprises a spacer domain between the half-docking domain and the stability domain, and the second oligonucleotide comprises a spacer domain between the half-docking domain and the stability domain.

18. The method of claim 11, wherein the half-docking domain of the first conjugate has a length of 5-15 nucleotides, and the half-docking domain of the second conjugate has a length of 5-15 nucleotides.

19. The method of claim 11, wherein the stability domain of the first conjugate has a length of 5-50 nucleotides, and the stability domain of the second conjugate has a length of 5-50 nucleotides.

20. The method of claim 11, wherein the detectably-labeled imager strand has a length of 10-30 nucleotides.

* * * * *

SEQUENCE LISTING

<160> NUMBER OF SEQ ID NOS: 7

<210> SEQ ID NO 1
<211> LENGTH: 9
<212> TYPE: DNA
<213> ORGANISM: Artificial Sequence
<220> FEATURE:
<223> OTHER INFORMATION: Synthetic Polynucleotide

<400> SEQUENCE: 1 gatgacatc                                                                 9

<210> SEQ ID NO 2
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 2
taataaggat                                                               10

<210> SEQ ID NO 3
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 3
ctaactaatt a                                                             11

<210> SEQ ID NO 4
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 4
atacaacgaa ctattcgtta gtttgttt                                           28

<210> SEQ ID NO 5
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 5
tatttagtgt tcgaatagtt cgatctag                                           28

<210> SEQ ID NO 6
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 6
atacaacgaa ctattcgtta gtttgttttt tt                                      32

<210> SEQ ID NO 7
<211> LENGTH: 32
<212> TYPE: DNA
<213> ORGANISM: Artificial Sequence

```
<220> FEATURE:
<223> OTHER INFORMATION: Synthetic Polynucleotide

<400> SEQUENCE: 7
tttttattta gtgttcgaat agttcgatct ag                              32
```